| United States Patent [19] | [11] Patent Number: 4,808,608 |
| Guindon et al. | [45] Date of Patent: Feb. 28, 1989 |

[54] TETRAHYDROCARBAZOLE 1-ALKANOIC ACIDS, PHARMACEUTICAL COMPOSITIONS AND USE

[75] Inventors: Yvan Guindon; Christiane Yoakim, both of Montreal; John W. Gillard, Baie d'Urfe; Yves Girard, Ile Bizard, all of Canada

[73] Assignee: Merck & Co., Inc., Rahway, N.J.

[21] Appl. No.: 76,424

[22] Filed: Jul. 21, 1987

Related U.S. Application Data

[63] Continuation-in-part of Ser. No. 001,739, Jan. 9, 1987, abandoned, which is a continuation-in-part of Ser. No. 821,726, Jan. 23, 1986, abandoned.

[51] Int. Cl.$^4$ .................. A61K 31/40; C07D 209/86; C07D 209/88
[52] U.S. Cl. ...................................... 514/411; 548/439
[58] Field of Search ...................... 548/439; 514/411

[56] References Cited

U.S. PATENT DOCUMENTS

| 3,896,145 | 7/1975 | Berger et al. | 548/444 |
| 4,009,181 | 2/1977 | Berger et al. | 548/439 |
| 4,057,559 | 11/1977 | Asselin et al. | 548/439 |

*Primary Examiner*—Robert W. Ramsuer
*Attorney, Agent, or Firm*—Hesna J. Pfeiffer; Charles M. Caruso

[57] ABSTRACT

Tetrahydrocarbazole 1-alkanoic acids are disclosed. The compounds act as prostaglandin and thromboxane antagonists and are useful in treating asthma, diarrhea, hypertension, angina, platelet aggregation, cerebral spasm, premature labor, spontaneous abortion and dysmenorrhea and as cytoprotective agents.

12 Claims, No Drawings

TETRAHYDROCARBAZOLE 1-ALKANOIC ACIDS, PHARMACEUTICAL COMPOSITIONS AND USE

RELATED CASES

This application is a continuation-in-part of U.S. Ser. No. 001,739, filed Jan. 9, 1987, now abandoned, which in turn is a continuation-in-part of U.S. Ser. No. 821,726, filed Jan. 23, 1986, now abandoned.

BACKGROUND OF THE INVENTION

This invention relates to prostaglandin antagonists useful in treating a variety of conditions, such as allergic asthma where excessive contractile activity of prostaglandins and prostaglandin biosynthetic intermediates occur.

These compounds antagonize the actions of contractile prostaglandins, such as $PGF_{2\alpha}$, $PGG_2$, $PGH_2$, $PGD_2$ and $TXA_2$. The use of agents which act as prostaglandin antagonists offers new approaches to therapy in a number of disease states. For example certain prostaglandins, such as $PGF_{2\alpha}$, $PGD_2$, $PGG_2$, and $PGH_2$, are potent bronchospastic agents. Indeed human asthmatics have been shown to be especially sensitive to the bronchial constricting action of $PGF_{2\alpha}$.

The compounds of the present invention are also antithrombotic agents. Thus, they are useful in the treatment and/or prevention of thromboembolic diseases such as arterial thrombosis and those involving platelet deposition, e.g. prothesis.

In addition to the involvement of contractile prostaglandins in asthma, prostaglandins are known to play a role in other allergic conditions, as well as, diarrhea, hypertension, angina, platelet aggregation, cerebral spasm, cerebral ischemia, arrythmia, circulatory shock, sudden death, atherosclerosis, myocardial ischemia, premature labor, spontaneous abortion, dysmenorrhea, glomerular nephritis, and systemic lupus erythematosis. Consequently, the compounds of this invention will alleviate the above mentioned diseases.

In addition to the prostaglandin antagonist actions, the compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene-related disease states.

The compounds of the present invention may be used to treat or prevent mammalian (especially, human) disease states such as erosive gastritis; erosive esophagitis; ethanol-induced hemorrhagic erosions; hepatic ischemia; noxious agent induced damage or necrosis of hepatic, pancreatic, renal, or myocardial tissue; liver parenchymal damage caused by hepatotoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

Certain 9-benzyl-1,2,3,4-tetrahydrocarbazole acetic acids or esters thereof are shown as chemical intermediates in the preparation of carbazoles that are known in the art as anti-inflammatory, analagesic and anti-rheumatic agents (see U.S. Pat. No. 3,896,145 and British Pat. No. 1,385,620). Certain 9-benzyl-1,2,3,4-tetrahydrocarbazole carboxylic acids are known in the art as anti-inflammatory, analgesic and anti-rheumatic agents (see U.S. Pat. Nos. 3,868,387; 4,009,181; 3,905,998 and 3,758,496), and 9-benzyl-carbazole carboxylic acids (U.S. Pat. Nos. 3,956,295 and 4,057,640) and 9-benzylcarbazole acetic acids and esters thereof (U.S. Pat. No. 3,896,145 and British Pat. No. 1,385,620) are known as anti-inflammatory, analgesic and anti-rheumatic agents. None of these compounds, however, are shown to be prostaglandin, or thromboxane antagonists or inhibitors of leukotrine biosynthesis.

DESCRIPTION OF THE INVENTION

The present invention relates to novel compounds of Formula I:

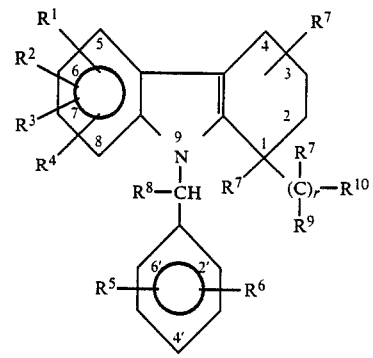

wherein:
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) $-(CH_2)_nM$
  wherein n is 0 to 3 and M is
  (a) $OR^{13}$;
  (b) halogen;
  (c) $CF_3$;
  (d) $SR^{13}$;
  (e) phenyl or substituted phenyl wherein substituted phenyl is as defined below in the definition of $R^{13}$;
  (f) $COOR^{14}$;
  (g)

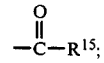

(h) tetrazole;
  (i)

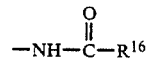

wherein $R^{16}$ is $C_1$ to $C_6$ alkyl, benzyl or phenyl;
  (j) $-NR^{14}R^{14}$;
  (k) $-NHSO_2R^{17}$ wherein $R^{17}$ is $C_1$ to $C_6$ alkyl, 4-methylphenyl, phenyl, or $CF_3$;
  (l)

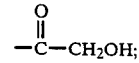

(m) —SOR$^{13}$;
(n) —CONR$^{14}$R$^{14}$;
(o) —SO$_2$NR$^{14}$R$^{14}$;
(p) —SO$_2$R$^{13}$;
(q) NO$_2$;
(r)

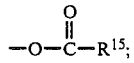

(s)

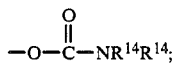

(t)

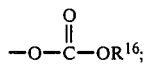

(v) N$_3$;
(u) CN;
R$^7$ is H or alkyl of 1 to 6 carbons;
R$^8$ is H or alkyl of 1 to 6 carbon atoms;
each R$^9$ is independently H, OH, C$_1$ to C$_4$-O-alkyl or alkyl of 1 to 4 carbons;
R$^{10}$ is COOH; CH$_2$OH; CHO; tetrazole; NHSO$_2$R$^{11}$ wherein R$^{11}$ is OH, alkyl or alkoxy of 1 to 6 carbons, perhaloalkyl of 1 to 6 carbons, phenyl or phenyl substituted by alkyl or alkoxy groups of 1 to 3 carbons, halogen, hydroxy, COOH, CN, formyl or acyl to 1 to 6 carbons; CONHSO$_2$R$^{11}$, hydroxymethylketone; CN; or CON(R$^9$)$_2$;
r is 1 to 6;
each R$^{13}$ independently is H; C$_1$ to C$_6$ alkyl; benzyl, phenyl or substituted phenyl wherein the substitents are C$_1$ to C$_3$ alkyl, halogen, CN, CF$_3$, COOR$^{14}$, CH$_2$COOR$^{14}$, C$_1$ to C$_3$ alkoxy, or C$_1$ to C$_4$ perfluoroalkyl;
each R$^{14}$ is independently H, phenyl, benzyl or C$_1$ to C$_6$ alkyl; and,
each R$^{15}$ independently is H, (CH$_2$)$_m$COOR$^{14}$ wherein m is 0 to 4, C$_1$ to C$_6$ alkyl, CF$_3$, phenyl, or substituted phenyl wherein substituted phenyl is as defined above in the definition of R$^{13}$;
or a pharmaceutically acceptable salt thereof.

As used herein, the terms "each independently" or the equivalents thereof are employed to describe a number of possible position isomers and/or structural variations. For example, as described above, the following unit is attached to position 1 of the tetrahydrocarbazole ring:

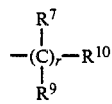

The letter r represents possible alkane chains of from 1 to 6 carbon atoms, each having the R$^7$ and R$^9$ substituent groups. On each carbon atom of the alkane chain, the R$^7$ and/or R$^9$ substituent may be different. The above description therefore contemplates structures such as the following for the segment —CR$^7$R$^9$)$_r$—:

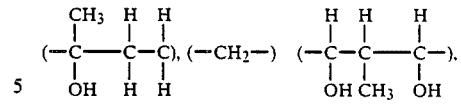

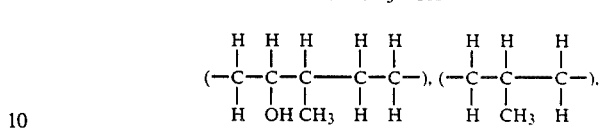

and the like.

If an R$^9$ is OH and R$^{10}$ is CO$_2$H, such compounds may form a lactone, and such lactones are to be regarded as part of the present invention.

The alkyl groups referred to above may be straight chain or branched or may include cycloalkyl groups. As used herein, the term "lower" as applied to alkyl, acyl, alkoxy and the like, unless stated otherwise refers to groups having 1 to 6 carbon atoms. Halogen or halo means fluoro, chloro, bromo and/or iodo.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium calcium and magnesium salts. Salts derived from pharmaceutically acceptable organic non-toxic bases include salts of primary, secondary, and tertiary amines, substituted amines including naturally occurring substitued amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylamino-ethanol, tomethamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethylmorpholine, polyamine resins and the like.

Preferred compounds of the present invention comprise the compounds of formula I wherein:
R$^1$, R$^2$, R$^3$, R$^4$, R$^5$ and R$^6$ are each independently selected from:
(1) hydrogen;
(2) alkyl having 1 to 6 carbon atoms;
(3) alkenyl having 2 to 6 carbon atoms;
(4) —(CH$_2$)$_n$M
wherein n is 0 or 1 and M is as defined previously for Formula I;
R$^{10}$ is COOH; CH$_2$OH; CHO; tetrazole; CONHSO$_2$R$^{11}$ wherein R$^{11}$ is OH, alkyl or alkoxy of 1 to 6 carbons, perhalogalkyl of 1 to 6 carbons, phenyl or phenyl substituted by alkyl or alkoxy groups of 1 to 3 carbons, halogen, hydroxy, COOH, CN, formyl or acyl to 1 to 6 carbons; hydroxymethylketone; CN; or CON(R$^9$)$_2$;
r is 1 to 6; and the remaining substituents are as defined previously for Formula I.

More preferred compounds of the present invention comprise the compounds of Formula I. wherein:

$R^1, R^2, R^3, R^4, R^5$ and $R^6$ are each independently selected from:
(1) hydrogen;
(2) alkyl having 1 to 6 carbon atoms;
(3) alkenyl having 2 to 6 carbon atoms;
(4) M wherein M is as defined initially for Formula I;
$R^{10}$ is COOH; $CH_2OH$; CHO; tetrazole; hydroxymethylketone;
r is 1 or 2; and the remaining substituents are as defined initially for Formula I.

Most preferred compounds of the present invention comprise the compounds of Formula I.
wherein:
$R^1, R^2, R^3, R^4, R^5$ and $R^6$ are each independently selected from:
(1) hydrogen;
(2) alkyl having 1 to 6 carbon atoms;
(3) M wherein M is
(a) $OR^{13}$;
(b) halogen;
(c) $CF_3$;
(d) $SR^{13}$;
(e) $COOR^{14}$;
(f)

(g) tetrazole;
(h) $-SOR^{13}$;
(i) $-CONR^{14}R^{14}$;
(j) $-SO_2NR^{14}R^{14}$;
(k) $-SO_2R^{13}$;
(l)

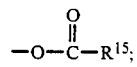

(m) CN;
(n) $N_3$;

each $R^9$ is independently H, or alkyl of 1 to 4 carbons;
$R^{10}$ is COOH; or tetrazole;
r is 1 and the remaining substituents are as defined initially for Formula I.

In the above most preferred embodiment, those compounds are particularly preferred wherein at least one of $R^1$ to $R^4$ is not hydrogen; one of $R^5$ or $R^6$ is not hydrogen; $R^7$ is hydrogen; $R^9$ is hydrogen, and the remaining substituents are as defined in the most preferred embodiment.

A further embodiment of the present invention are the following novel compounds (Table 1). Among the resolved isomers in Table 1 the (−) isomers, compounds 3, 37, 39, 41 and 63 are preferred.

TABLE 1

Novel Tetrahydrocarbazole Alkanoic Acids

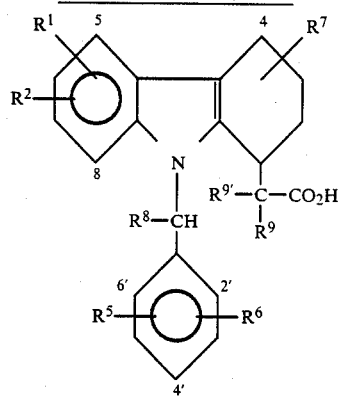

| Compound | $R^1$ | $R^2$ | $R^5$ | $R^6$ | $R^9, R^{9'}$ | $R^7$ | $R^8$ |
|---|---|---|---|---|---|---|---|
| 1 (Ex. 1) | 6-F | H | 4'-Cl | H | H, H | H | H |
| 2 (Ex. 4) | 6-OMe | H | 4'-Cl | H | H, H | H | H |
| 3 (Ex. 7) | 6-F (−) isomer | H | 4'-Cl | H | H, H | H | H |
| 4 (Ex. 8) | 6-F (+) isomer | H | 4'-Cl | H | H, H | H | H |
| 5 (Ex. 9) | 6-F | H | H | H | H, H | H | H |
| 6 (Ex. 10) | 6-F | H | 4'-OMe | H | H, H | H | H |
| 7 (Ex. 11) | 6-F | H | 3'-Cl | 4'-Cl | H, H | H | H |
| 8 (Ex. 12) | 6-F | H | H | H | H, H | H | Me |
| 9 (Ex. 13) | H | H | 4'-Cl | H | H, H | H | H |
| 10 (Ex. 14) | 6-Cl | H | 4'-Cl | H | H, H | H | H |
| 11 (Ex. 15) | 8-Me | H | 4'-Cl | H | H, H | H | H |
| 12 (Ex. 16) | 6-Br | H | 4'-Cl | H | H, H | H | H |
| 13 (Ex. 17) | 6-Me | H | 4'-Cl | H | H, H | H | H |
| 14 (Ex. 19) | 8-F | H | 4'-Cl | H | H, H | H | H |
| 15 (Ex. 20) | 6-F | H | 4'-Cl | H | H, H | 3-t-Bu | H |
| 16 (Ex. 21) | 5-F | H | 4'-Cl | H | H, H | H | H |
| 17 (Ex. 21) | 7-F | H | 4'-Cl | H | H, H | H | H |
| 18 (Ex. 22) | 5-Cl | 7-Cl | 4'-Cl | H | H, H | H | H |
| 19 (Ex. 23) | 6-Cl | 8-Cl | 4'-Cl | H | H, H | H | H |
| 20 (Ex. 18) | 6-F | H | 4'-Cl | H | Me, H | H | H |
| 21 | 6-F | H | 4'-Cl | H | Me, Me | H | H |

TABLE 1-continued

Novel Tetrahydrocarbazole Alkanoic Acids

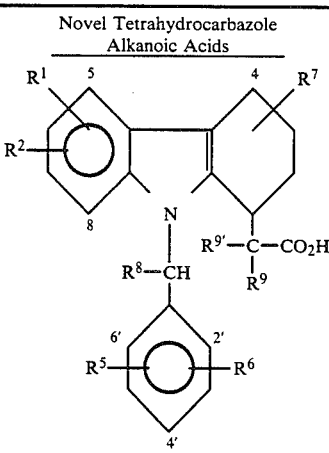

| Compound | $R^1$ | $R^2$ | $R^5$ | $R^6$ | $R^9, R^{9'}$ | $R^7$ | $R^8$ |
|---|---|---|---|---|---|---|---|
| 22 | 6-F | H | 4'-Cl | H | H, H | 1-Me | H |
| 23 | 8-Br | H | 4'-Cl | H | H, H | H | H |
| 24 (Ex. 24) | 6-CH(Me)$_2$ | H | 4'-Cl | H | H, H | H | H |
| 25 (Ex. 25) | 6-C(Me)$_3$ | H | 4'-Cl | H | H, H | H | H |
| 26 (Ex. 26) | 6-CF$_3$ | H | 4'-Cl | H | H, H | H | H |
| 27 (Ex. 27) | 6-SMe | H | 4'-Cl | H | H, H | H | H |
| 28 (Ex. 28) | 6-S(O)Me | H | 4'-Cl | H | H, H | H | H |
| 29 (Ex. 29) | 6-S(O)$_2$Me | H | 4'-Cl | H | H, H | H | H |
| 30 (Ex. 30) | 8-CH(Me)$_2$ | H | 4'-Cl | H | H, H | H | H |
| 31 (Ex. 31) | 8-SMe | H | 4'-Cl | H | H, H | H | H |
| 32 (Ex. 32) | 8-S(O)Me | H | 4'-Cl | H | H, H | H | H |
| 33 (Ex. 33) | 6-F | H | 4'-Cl | H | H, H | 3-Me | H |
| 34 (Ex. 34) | 6-F | 8-F | 4'-Cl | H | H, H | H | H |
| 35 (Ex. 35) | 6-Me | 8-Me | 4'-Cl | H | H, H | H | H |
| 36 (Ex. 36) | 6-OMe | 8-Me | 4'-Cl | H | H, H | H | H |
| 37 (Ex. 37) | 6-F(−)Isomer | 8-F | 4'-Cl | H | H, H | H | H |
| 38 (Ex. 38) | 6-F(+)Isomer | 8-F | 4'-Cl | H | H, H | H | H |
| 39 (Ex. 39) | 8-Me(−)Isomer | H | 4'-Cl | H | H, H | H | H |
| 40 (Ex. 40) | 8-M3(+)Isomer | H | 4'-Cl | H | H, H | H | H |
| 41 (Ex. 41) | 8-F(−)Isomer | H | 4'-Cl | H | H, H | H | H |
| 42 (Ex. 42) | 8-F(+)Isomer | H | 4'-Cl | H | H, H | H | H |
| 43 | 6-F | 8-F | 3'-Cl | 4'-Cl | H, H | H | H |
| 44 (Ex. 46) | 6-F | 8-F | 2'-Cl | 4'-Cl | H, H | H | H |
| 45 | 6-F | 8-F | 4'-OMe | H | H, H | H | H |
| 46 | 6-F | 8-F | 4'-OH | H | H, H | H | H |
| 47 (Ex. 47) | 6-F | 8-F | 4'-SMe | H | H, H | H | H |
| 48 | 6-F | H | 4'-S(O)Me | H | H, H | H | H |
| 49 (Ex. 59) | 6-F | 8-F | 4'-NHCOMe | H | H, H | H | H |
| 50 | 6-F | H | 4'S(O)$_2$Me | H | H, H | H | H |
| 51 | 6-F | H | 4'F | H | H, H | H | H |
| 52 | 6-F | H | 4'-Br | H | H, H | H | H |
| 53 | 6-F | 8-Me | 4'-Cl | H | H, H | H | H |
| 54 | 6-F | H | 4'-CO$_2$H | H | H, H | H | H |
| 55 | 6:F | H | 4'-CO$_2$Me | H | H, H | H | H |
| 56 | 6-F | 8-F | 4'-n-C$_3$H$_7$ | H | H, H | H | H |
| 57 | 6-F | 8-F | 3'-I | 4'-OH | H, H | H | H |
| 58 | 6-F | 8-F | 4'-I | H | H, H | H | H |
| 59 | 6-N$_3$ | H | 4'-Cl | H | H, H | H | H |
| 60 | 6-F | H | 4'-N$_3$ | H | H, H | H | H |
| 61 (Ex. 48) | 6-F | 8-F | 4'-S(O)Me | H | H, H | H | H |
| 62 (Ex. 49) | 6-F | 8-F | 4'-S(O)$_2$Me | H | H, H | H | H |
| 63 (Ex. 50) | 6-F(−)isomer | 8-F | 4'-S(O)$_2$Me | H | H, H | H | H |
| 64 (Ex. 51) | 6-F(+)isomer | 8-F | 4'-S(O)$_2$Me | H | H, H | H | H |
| 65 (Ex. 45) | 6-F | 8-F | 2'-Cl | H | H, H | H | H |
| 66 (Ex. 52) | 6-F | 8-F | 4'-CF$_3$ | H | H, H | H | H |
| 67 (Ex. 53) | 6-F | 8-F | 4'-F | H | H, H | H | H |
| 68 (Ex. 54) | 6-F | 8-F | 3'-Cl | H | H, H | H | H |
| 69 (Ex. 55) | 6-F | 8-F | 4'-CO$_2$Me | H | H, H | H | H |
| 70 (Ex. 56) | 6-F | 8-F | 4'-CONME$_2$ | H | H, H | H | H |
| 71 (Ex. 57) | 6-F | 8-F | 4'COMe | H | H, H | H | H |
| 72 (Ex. 58) | 6-F | 8-F | 4'-SO$_2$NMe$_2$ | H | H, H | H | H |
| 73 (Ex. 60) | 6-F | 8-F | 4'-NHSO$_2$Me | H | H, H | H | H |
| 74 (Ex. 61) | 6-F | 8-F | 4'-NHCONHMe | H | H, H | H | H |
| 75 (Ex. 62) | 6-F | 8-F | 4'-OMe | H | H, H | H | H |
| 76 | 6-F | 8-F | 4'-CO$_2$H | H | H, H | H | H |
| 77 | 6-F | 8-F | 4'-NH$_2$ | H | H, H | H | H |
| 78 | 6-F | 8-F | 4'-OH | H | H, H | H | H |

TABLE 1-continued
Novel Tetrahydrocarbazole Alkanoic Acids

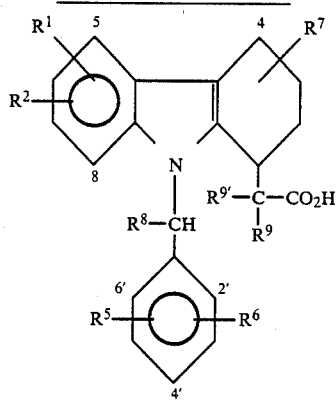

| Compound | $R^1$ | $R^2$ | $R^5$ | $R^6$ | $R^9, R^{9'}$ | $R^7$ | $R^8$ |
|---|---|---|---|---|---|---|---|
| 79 | 6-F | 8-F | | 4'-OCH$_2$CO$_2$H | H, H | H | H |

The following reaction schemes illustrate the preparation of the compounds of the present invention:

Scheme I
Preparation of Formula I Compounds

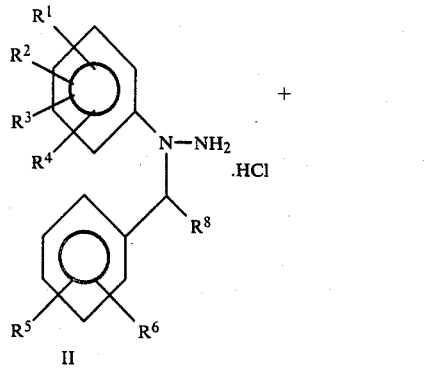

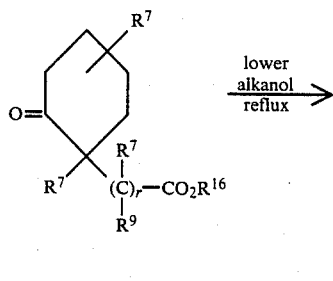

The reaction can be conveniently carried out in an alcohol solvent such as t-butanol, i-butanol, and the like. The hydrolysis of the ester intermediates IIIa is conveniently carried out by using NaOH or KOH in aqueous ethanol or methanol followed by acidification to obtain compounds of Formula I.

The following ketones (1, 2, 4) of structure III are known in the art, and ketones 3 and 5 are readily prepared by procedures analogous to those for the known ketones.

TABLE 2
ketones of Formula III

| No. | Structure | Reference |
|---|---|---|
| 1. | (cyclohexanone with CH2CO2Et) | Ethyl 2-cyclohexanone acetate; commercially available (Aldrich) |
| 2. | (cyclohexanone with CH2CH2CO2Me) | Methyl 2-cyclohexanone propionate; J.A.C.S. 85 207 (1963) G. Stork, A. Brizzolara, H. Landesman, J. Scmuszkovicz and R. Terrell |
| 3. | (4-t-butyl cyclohexanone with CH2CO2Me) | Methyl 4-t-butyl-2-cyclohexanone acetate |
| 4. | (cyclohexanone with CH(CH3)CO2Me) | Methyl 2-(2-cyclohexanone) propionate J.A.C.S. 85 207 (1963) G. Stork, A. Brizzolara, H. Landesman, J. Scmuszkovicz and R. Terrell |
| 5. | (4-methyl cyclohexanone with CH2CO2Et) | Ethyl 4-methyl-2-cyclohexanone acetate |

The sequence described above is an application of the Fischer Indole Synthesis. Numerous-indole syntheses are described in reviews, such as, for example "Heterocyclic Compounds" Volume 25, Parts I, II, III, W. J. Houlihan (Ed.), Interscience, J. Wiley & Sons, N.Y., 1979. Appropriate manipulations of functional groups using sequences described in such reviews will lead to the compounds of the present invention.

Scheme II
Preparation of Hydrazine Derivatives (II)

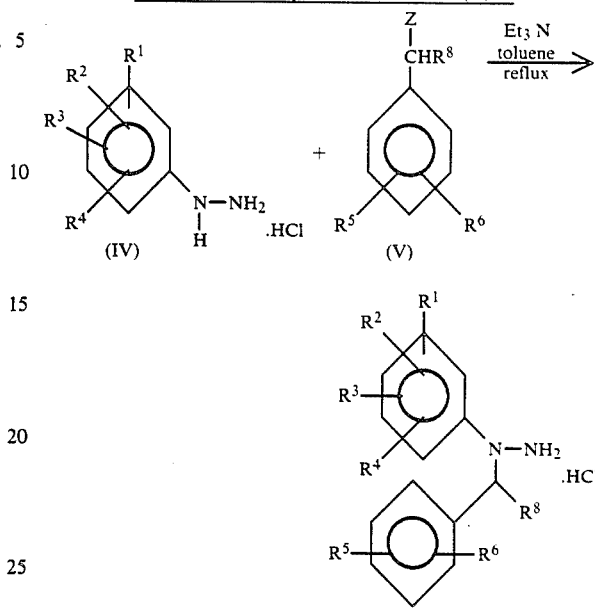

Z is a leaving group such as Cl, Br, I, mesylate or tosylate

With regard to Scheme II, the preparation of hydrazine starting materials is illustrated by the preparation of 1-(4-chlorobenzyl)-1-(4-methoxyphenyl)hydrazine. A mixture of 10 g of p-methoxyphenylhydrazine hydrochloride, 75 ml of toluene and 11.5 ml of triethylamine was heated at reflux for 60 minutes. Then, 7.1 g of p-chlorobenzyl chloride was added. After stirring 16 hours at reflux, triethylamine hydrochloride was filtered off and washed with ethyl ether. The filtrate and washing were concentrated in vacuo and chromatographed on a silica gel column (hexane-ethyl acetate, 9:1) to give 6.64 g of 1-(4-chlorobenzyl)-1-(4-methoxyphenyl)hydrazine. Other hydrazines, similarly prepared, are also shown in Table 3, below.

Examples of benzyl halides V are shown in Table 3b.

TABLE 3
Hydrazines

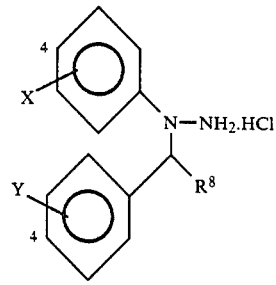

| Compound No. | X | Y | $R^8$ | Compound Name |
|---|---|---|---|---|
| 1. | 4-F | 4-Cl | H | 1-(4-chlorobenzyl)-1-(4-fluorophenyl) hydrazine hydrochloride |
| 2. | 3,5-$Cl_2$ | 4-Cl | H | 1-(4-chlorobenzyl)-1-(3,5-dichlorophenyl)hydrazine |

TABLE 3-continued

Hydrazines

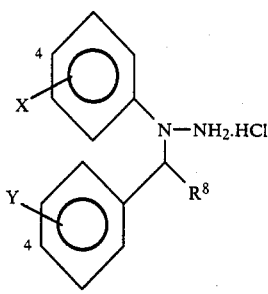 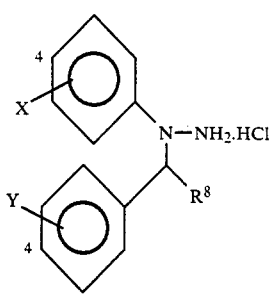

| Compound No. | X | Y | R⁸ | Compound Name |
|---|---|---|---|---|
| 3. | 4-OMe | 4-Cl | H | 1-(4-chlorobenzyl)-1-(4-methoxyphenyl) hydrazine hydrochloride |
| 4. | 2-Me | 4-Cl | H | 1-(4-chlorobenzyl)-1-(2-methylphenyl) hydrazine hydrochloride |
| 5. | 3-Me | 4-Cl | H | 1-(4-chlorobenzyl)-1-(4-methylphenyl) hydrazine hydrochloride |
| 6. | 4-Cl | 4-Cl | H | 1-(4-chlorobenzyl)-1-(4-chlorophenyl) hydrazine hydrochloride |
| 7. | H | 4-Cl | H | 1-(4-chlorobenzyl)-1-(phenyl) hydrazine hydrochloride |
| 8. | 4-Br | 4-Cl | H | 1-(4-chlorobenzyl)-1-(4-bromophenyl) hydrazine hydrochloride |
| 9. | 3-F | 4-Cl | H | 1-(4-chlorobenzyl)-1-(3-fluorophenyl) hydrazine hydrochloride |
| 10. | 2,4-Cl₂ | 4-Cl | H | 1-(4-chlorobenzyl)-1-(2,4-dichlorophenyl) hydrazine hydrochloride |
| 11. | 4-F | H | H | 1-(benzyl)-1-(4-fluorophenyl) hydrazine hydrochloride |
| 12. | 4-F | 4-OMe | H | 1-(4-methoxybenzyl)-1-(4-fluorophenyl) hydrazine hydrochloride |
| 13. | 4-F | 3,4-Cl₂ | H | 1-(3,4-dichlorobenzyl)-1-(4-fluoro-phenyl) hydrazine hydrochloride. |
| 14. | 4-F | H | CH₃ | 1-[1-(phenyl)ethyl]-1-(4-fluorophenyl) hydrazine hydrochloride |
| 15. | 2-F | 4-Cl | H | 1-(4-chlorobenzyl)-1-(2-fluorophenyl) hydrazine hydrochloride. |
| 16. | | | | 1-[2-(4-chlorophenyl)ethyl]-1-(4-fluorophenyl) hydrazine hydrochloride. |
| 17. | | | | 1-(2-propyl)-1-(4-fluorophenyl)hydrazine hydrochloride. |
| 18. | 4-CH(Me)₂ | 4-Cl | H | 1-(4-chlorobenzyl)-1-(4-isopropylphenyl)hydrazine hydrochloride |
| 19. | 4-C(Me)₃ | 4-Cl | H | 1-(4-chlorobenzyl)-1-(4-tert-butylphenyl)hydrazine)hydrochloride |
| 20. | 4-CF₃ | 4-Cl | H | 1-(4-chlorobenzyl)-1-(4-trifluoromethylphenyl)-hydrazine hydrochloride |
| 21. | 4-SMe | 4-Cl | H | 1-(4-chlorobenzyl)-1-(4-methylthiophenyl)hydrazine hydrochloride |
| 22. | 2-CH(Me)₂ | 4-Cl | H | 1-(4-chlorobenzyl)-1-(2-isopropylphenyl)hydrazine hydrochloride |

Scheme III
Alternative Preparation of Formula I Compounds

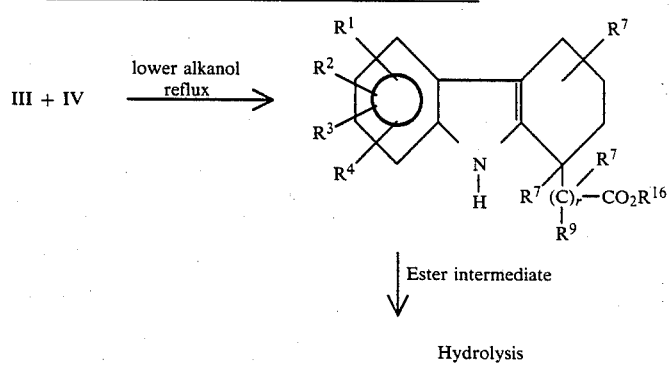

-continued
Scheme III
Alternative Preparation of Formula I Compounds

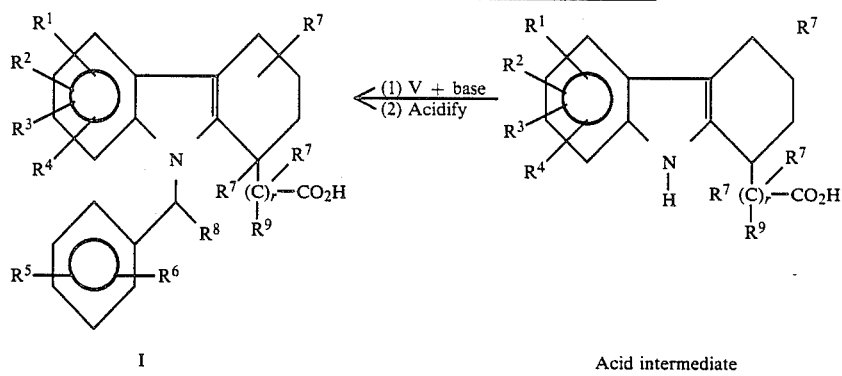

I           Acid intermediate

Scheme III illustrates an alternative synthesis of the compounds of Formula I. In this Scheme a Fischer indole synthesis is carried out using a phenylhydrazine IV and the ketone III, followed by hydrolysis. The acid intermediate is then N-benzylated with the reagent V, preferably using a strong base such as potassium t-butoxide, sodium hydride (NaH) or potassium hexamethyldisilazide (KHMDS) to effect the reaction. Acidification of the reaction mixture then yields the free acid of I.

Scheme IV
Preparation of Sulfoxides and Sulfones of Formula I Compounds

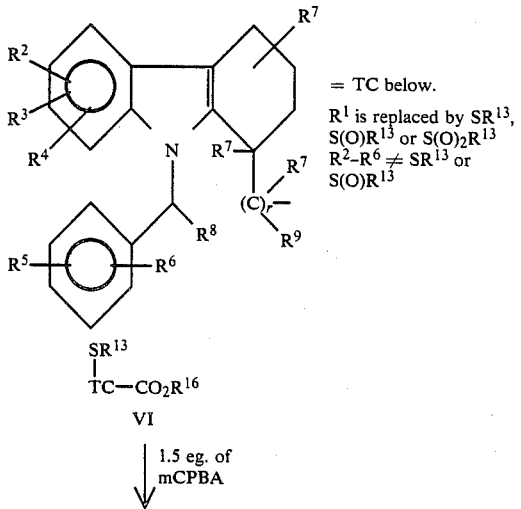

-continued
Scheme IV
Preparation of Sulfoxides and Sulfones of Formula I Compounds

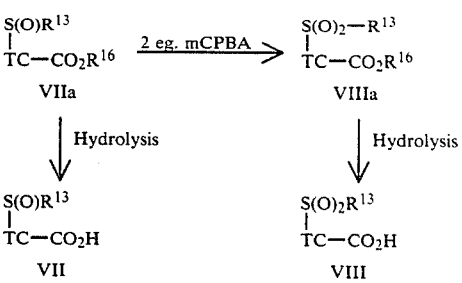

In Scheme IV is illustrated a method of preparing derivatives of Formula I in which one of the substituents among $R^1$-$R^4$ is a sulfoxide or a sulfone. It will be obvious to one skilled in the art that a sulfoxide or sulfone derivative or $R^5$ or $R^6$ could be prepared in the same way.

Ester VI (a representative of IIIa, Scheme I) is prepared according to Scheme I or Scheme III followed by esterification of acid I. Treatment of VI with a limited amount of an oxidizing agent such as m-chloro-perbenzoic acid yields the sulfoxide ester VIIa, which upon hydrolysis yields sulfoxide acid VII. Further treatment of VIIa with the oxidizing agent, or treatment of VI with an excess (>2 eq.) of the oxidizing agent yields the sulfone ester VIIIa, hydrolysis of which yields the sulfone acid VIII. Both VII and VIII are representatives of Formula I compounds.

Scheme V
Preparation of Further compounds of Formula I

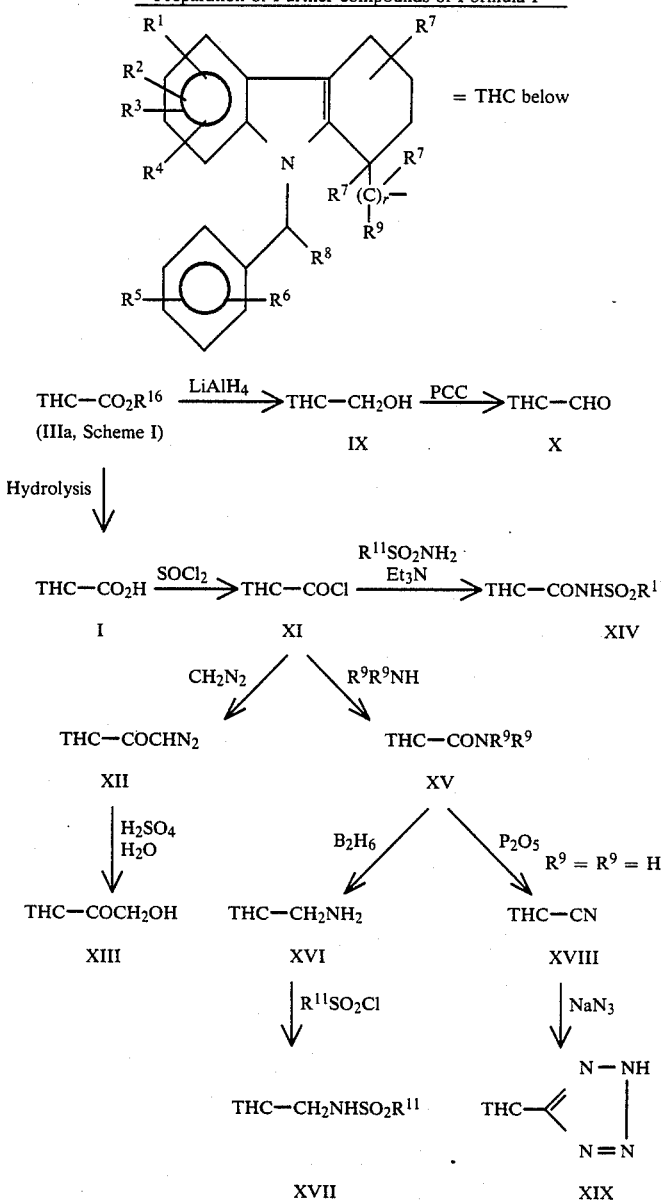

Other compounds of Formula I can be prepared as indicated in Scheme V. Thus the ester derivative IIIa can be reduced to the alcohol IX by lithium aluminum hydride or other suitable reducing agents. Alcohol IX can then be oxidized to aldehyde X by pyridinium chlorochromate or other suitable oxidizing agents. Carboxylic acids of Formula I can be converted to the acid chloride XI (the acid bromide or a mixed carbonate anhydride could also be used) which when reacted with diazomethane yields the diazoketone XII. Compound XII, upon reaction with aqueous acid, preferably a non-nucleophilic acid such as sulfuric acid or p-toluenesulfonic acid, is converted to the hydroxymethyl ketone XIII.

Acid chloride XI, upon reaction with a sulfonamide, $R^{11}SO_2NH_2$, in the presence of a weak base yields the acyl-sulfonamide XIV. Reaction of XI with an amine, $R^9R^9NH$, yields amide XV. Amide XV can be sequentially reduced, to amine XVI, with diborane or lithium aluminum hydride, and sulfonylated with $R^{11}SO_2Cl$ to produce sulfonamide XVII. Amide XV (when both $R^9$ substituents are hydrogen) can be dehydrated by standard reagents to nitrile XVIII, which is converted to tetrazole XIX by reaction with sodium azide, tri-n-butyltin azide or other suitable methods. Compounds IX, X, XIII, XIV, XV, XVII, XVIII and XIX are representatives of Formula I compounds.

Scheme VI
Preparation of Hydrazine Derivatives IV

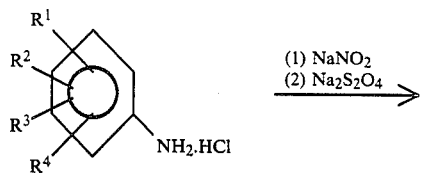

With regard to Scheme VI, the preparation of hydrazine starting materials is illustrated by preparation of 4-methylthiophenyl hydrazine hydrochloride. 4-Methylthioaniline (13.9 g) was added dropwise to cold HCl (6N) (50 mL) and stirred for 5 min in an ice bath. A solution of $NaNO_2$ in water (7.25 g, 15 mL) was then added dropwise and stirred for 15 min. The cold diazonium salt was then cannulated into a stirred cold solution of $Na_2S_2O_4$ in water (50 g, 250 mL). After 20 min, ether (200 mL) was added and the reaction mixture basified with NaOH (10N). The ether layer was decanted, washed with brine, dried over $Na_2SO_4$ and HCl gas was passed through the ether solution to form the hydrochloride salt which precipitated out. After filtration, there was obtained 7.0 g of pure final product. Other hydrazines, similarly prepared, are also shown in Table 4, below.

TABLE 3a
HYDRAZINES

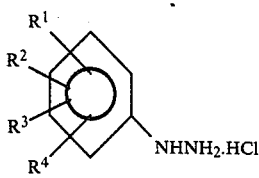

| No. | $R^1$ | $R^2$ | Compound Name |
|---|---|---|---|
| 1 | 4-SMe | H | 4-methylthiophenyl hydrazine hydrochloride |
| 2 | 2-CH(Me)$_2$ | H | 2-isopropylphenyl hydrazine hydrochloride |
| 3 | 2-SMe | H | 2-methylthiophenyl hydrazine hydrochloride |
| 4 | 2-Me | 4-Me | 2,4-dimethylphenyl hydrazine hydrochloride |
| 5 | 2-Me | 4-OMe | 4-methoxy-2-methylphenyl hydrazine hydrochloride |

TABLE 3b
Benzyl Halides V

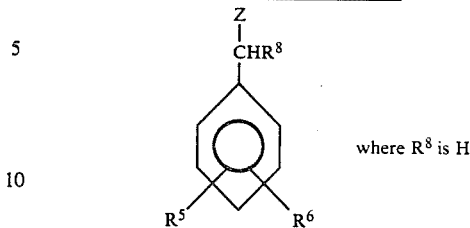

where $R^8$ is H

| Compound No. | Z | $R^5$ | $R^6$ | Compound Name |
|---|---|---|---|---|
| 1. | Cl | 4-Cl | H | 4-chlorobenzyl chloride (ALDRICH) |
| 2. | Cl | 4-OMe | H | 4-methoxybenzyl chloride (ALDRICH) |
| 3. | Cl | 2-Cl | 4-Cl | 2,4-dichlorobenzyl chloride (ALDRICH) |
| 4. | Br | 2-Cl | H | 2-chlorobenzyl bromide (ALDRICH) |
| 5. | Br | 3-Cl | H | 3-chlorobenzyl bromide (ALDRICH) |
| 6. | Br | 4-F | H | 4-fluorobenzyl bromide (ALDRICH) |
| 7. | Br | 4-CF$_3$ | H | 4-trifluoromethylbenzyl bromide (ALDRICH) |
| 8. | Cl | 4-CO$_2$Me | H | 4-carbomethoxybenzyl chloride (J.A.C.S. 1950, 72 5152) |
| 9. | Cl | 4-SMe | H | 4-methylthiobenzyl chloride (C.A.: 56: 4774 (1962)) |
| 10. | Cl | 4-SOMe | H | 4-methylsulfinyl- benzyl chloride (C.A.: 84: 104277h (1976)) |
| 11. | Cl | 4-SO$_2$Me | H | 4-methylsulfonylbenzyl chloride (C.A.: 78: 1113259 (1973)) |
| 12. | Br | 4-NO$_2$ | H | 4-nitrobenzyl bromide (ALDRICH) |
| 13. | Cl | 4-CONMe$_2$ | H | 4-dimethylcarboxamidobenzyl chloride |
| 14. | Cl | 4-SO2NMe$_2$ | H | 4-dimethylaminosulfonylbenzyl chloride (C.A.: 84: 135484r (1976)) |
| 15. | Cl | 4-CO$_2$H | H | 4-carboxybenzyl chloride (ALDRICH) |
| 16. | Cl | 4-COMe | H | 4-acetylbenzyl chloride (C.A.: 93: 2399945 (1980)) |

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The prostaglandin antagonist properties of the compounds of the present invention can be demonstrated by a number of biological assays, two of which, inhibition of platelet aggregation and measurement of $pA_2$ valves are described below.

INHIBITION OF INDUCED THRESHOLD AGGREGATION OF HUMAN PLATELETS

Human platelet rich plasma (PRP) is prepared from venous blood of male volunteers who have taken no medication for ten days prior to test. Blood is transferred into plastic centrifuge tubes containing 3.8% Trisodium Citrate in 0.9% NaCl (in a ratio of blood to anticoagulant of 9:1), mixed by gentle inversion, and centrifuged at room temperature for ten minutes at 116 g. The supernatant (PRP) is transferred into plastic tubes. Platelet poor plasma (PPP) is obtained by centrifuging the residual blood cells at 4000 g for ten minutes. PRP is left to stand at least one half hour prior to testing.

Platelet Aggregation is measured using a Payton Aggregometer and Recorder. Following calibration of the instrument, a cuvette containing PRP (225 microliters) is incubated for three minutes at 37° C. Drug vehicle (control), or a drug concentration is then added in a volume of 0.5 microliter. After one minute, the aggregating agent (U44069, 9,11-dideoxy-9α,11α-epoxymethano $PGF_{2\alpha}$) is added to the cuvette in a volume of 25 microliters. Recording is continued until the maximal response is obtained.

The threshold (approximately 20-30% of maximum) aggregation concentration of the agonist to be used is first determined in the presence of the drug vehicle (control). Test compounds are then assayed at 10 or 30 micrograms/ml initially, and if active, are further tested in order to determine the concentration range at which 20-80% of the threshold aggregatory response is inhibited. All drugs are dissolved in dimethylsulfoxide.

The height of the aggregation response (measured in divisions of the recorder paper, 1 division = 2.5 mm) in the presence of the drug is recorded, and calculated as percent inhibition of the mean height of the control threshold responses. The $IC_{50}$ (drug concentration which inhibits 50% of the aggregatory response) is obtained by regression analysis.

ESTIMATION OF $pA_2$ VALUES IN GUINEA PIG TRACHEAL CHAIN

Male albino Hartley strain guinea pigs (300-350 gm) were sacrificed by a blow to the head and exsanguinated. The trachea was removed, freed of extraneous tissue and sectioned into rings of 1-2 mm thickness. Five rings were tied together in series, ensuring that the tracheal muscle lay in the same vertical plane, and the cartilage of each ring then separated at a point directly opposite the muscle. The chains were suspended under 1 gm resting tension in modified Krebs solution (NaCl, 6.87; $NaHCO_3$, 2.1; dextrose, 2.1; KCl, 0.31; $CaCl_2$, 0.28; $MgSO_4$, $7H_2O$, 0.11; $KH_2PO_4$, 0.16; gm/L: equilibrated with 5% $CO_2$ in $O_2$ for 1 hour) containing indomethacin ($1.4 \times 10^{-5}$M) to suppress endogenous protaglandin synthesis, Organ bath temperature was maintained at 37° C. and 5% $CO_2$ in $O_2$ diffused continuously. Isometric tension changes were recorded from a Gould-Statham (UTC 2) force displacement transducer connected to a Beckman Type R Dynograph. For assay purposes initial maximal contractions were elicited with a high concentration of the contractile agonist [U-44069, 9.11-dideoxy-9α,11α-epoxymethano $PGF_{2\alpha}$] and the tissue subsequently washed at intervals until tension returned to baseline. Agonist dose response curves were obtained using a cumulative-dose schedule (4-8 doses) and the preparations then washed at regular intervals until baseline tension was recorded. After an appropriate interval (1-1.5 hrs) agonist dose response curves were repeated in the presence of antagonist drug concentrations. Drug doses were delivered in 10 μl volumes 5 minutes prior to the second agonist challenge, and cumulative agonist volumes did not exceed 100 μl per bath. $EC_{50}$ values were obtained by regression analysis and used to calculate 'apparent' and Schild Plot $pA_2$ values by the method of Tallarida and Murray 1981.

Compounds of Formula I can be tested using the following assay to determine their mammalian leukotriene biosynthesis inhibiting activity.

RAT PERITONEAL POLYMORPHONUCLEAR (PMN) LEUKOCYTE ASSAY

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered, through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on he gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP No. 140,684.

In Table 4 below are presented data indicating the prostanoid antagonist activities of compounds of the present invention indicated in Table 1. It is to be noted that $pA_2$ values are on a logarithmic scale, so that, for instance, a difference between two $pA_2$ values of 1 represents a difference in potency by a factor of 10.

Compounds A, B, C and D in Table 4 are known in the art: U.S. Pat. No. 3,896,145 describes compounds A and C, U.S. Pat. No. 3,868,387 describes compound B, and compound D is described in U.S. Pat. No. 3,905,998.

Compound A, which is a positional isomer of the novel compound 2, is nevertheless almost 12 times less potent as an inhibitor of platelet aggregation and its $pA_2$ is a factor of 14 (antilog of 1.6) less than that of compound 2. The homolog B, with one carbon less than A, shows no sigificant activity. Also of interest is the fact that the fully aromatic carbazole analog of the novel compound 2, compound C, does not possess any significant activity. Compounds D and E, isomeric with compound B further demostrate that direct attachment of the carboxyl group to the tetrahydrocarbazole nucleus results in severe loss of activity.

Compound 8 indicates an interesting differentiation of prostaglandin antagonist activity, depending upon the tissue, with very weak action on the guinea pig trachea (pA$_2$ 6), but with very good potency as an inhibitor of human platelet aggregation (IC$_{50}$=0.09 μg/ml).

Compound F demonstrates that a hydrogen atom attached to the 9-position (the nitrogen atom) results in severe loss of activity. Likewise, compound G, with a 9-alkyl substituted, has almost completely lost activity. Compound H, with a 2-phenylethyl substituent at the 9-position has also suffered a serious loss of activity by the addition of a CH$_2$ group compared to Compound 1. The last three compounds (F, G and H) demonstrate the requirement for a benzyl or substituted benzyl group at position-9 in the compounds of the present invention.

TABLE 4

| | Compound | Inhibition of platelet aggregation (IC$_{50}$ in μg/ml) | pA$_2$ |
|---|---|---|---|
| A | 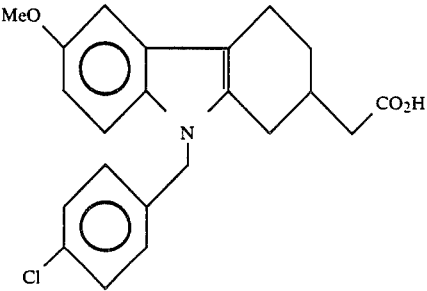 | 3.5 | 6.8 |
| B | 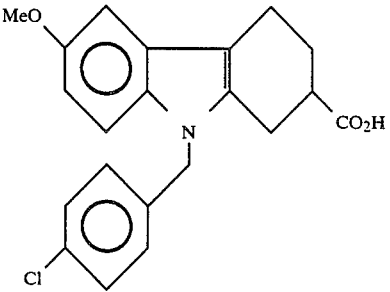 | >30 | <6.8 |
| C | 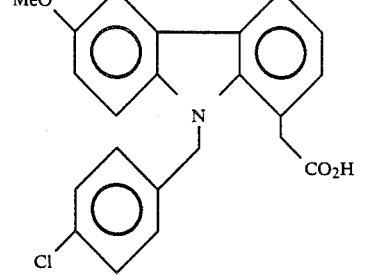 | >30 | 6.58 |
| D | 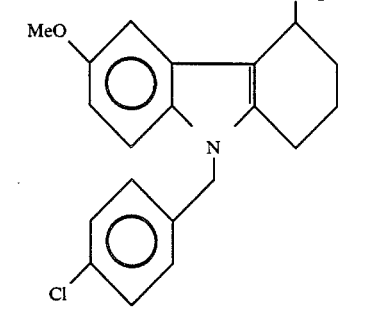 | | <6 |

TABLE 4-continued

Prostanoid Antagonist Activities

| Compound | Inhibition of platelet aggregation (IC$_{50}$ in μg/ml) | pA$_2$ |
|---|---|---|
| E | 4.23 | 6.66 |
| F | 3.41 | <6 |
| G | 13.6 | <6 |
| H | 13.6 | 6.8 |
| I | 0.03 | 8.6 |

TABLE 4-continued
Prostanoid Antagonist Activities

| Compound | | Inhibition of platelet aggregation ($IC_{50}$ in µg/ml) | $pA_2$ |
|---|---|---|---|
| 2 | 4-MeO-phenyl / N-(4-chlorobenzyl) indene cyclohexyl-CO₂H | 0.30 | 8.4 |
| 3 | 4-F-phenyl / N-(4-chlorobenzyl) indene cyclohexyl-CO₂H | 0.05 | 8.0 |
| 6 | 4-F-phenyl / N-(4-methoxybenzyl) indene cyclohexyl-CO₂H | 0.15 | 8.7 |
| 7 | 4-F-phenyl / N-(3,4-dichlorobenzyl) indene cyclohexyl-CO₂H | 0.09 | 8.3 |
| 8 | 4-F-phenyl / N-(1-phenylethyl) indene cyclohexyl-CO₂H | 0.09 | <6 |

TABLE 4-continued

Prostanoid Antagonist Activities

| Compound | | Inhibition of platelet aggregation (IC$_{50}$ in μg/ml) | pA$_2$ |
|---|---|---|---|
| 9 | [indole with N-CH$_2$-(4-Cl-phenyl), fused cyclohexene bearing CH$_2$CO$_2$H] | 0.05 | 8.9 |
| 10 | [5-Cl-indole with N-CH$_2$-(4-Cl-phenyl), fused cyclohexene bearing CH$_2$CO$_2$H] | 0.10 | 8.0 |
| 11 | [7-Me-indole with N-CH$_2$-(4-Cl-phenyl), fused cyclohexene bearing CH$_2$CO$_2$H] | 0.10 | 9.5 |
| 12 | [5-Br-indole with N-CH$_2$-(4-Cl-phenyl), fused cyclohexene bearing CH$_2$CO$_2$H] | 0.09 | 7.9 |
| 13 | [6-Me-indole with N-CH$_2$-(4-Cl-phenyl), fused cyclohexene bearing CH$_2$CO$_2$H] | 0.08 | 7.6 |

TABLE 4-continued

Prostanoid Antagonist Activities

| Compound | | Inhibition of platelet aggregation (IC$_{50}$ in µg/ml) | pA$_2$ |
|---|---|---|---|
| 14 | (structure: 4-F indole, N-CH$_2$-(4-Cl-phenyl), fused cyclohexene with CO$_2$H) | 0.08 | 9.4 |
| 16 | (structure: 4,6-di(F) indole, N-CH$_2$-(4-Cl-phenyl), fused cyclohexene with CO$_2$H) | 0.17 | 8.9 |
| 19 | (structure: 4,5-di-Cl indole, N-CH$_2$-(4-Cl-phenyl), fused cyclohexene with CO$_2$H) | 0.07 | 7.2 |
| 20 | (structure: 4-F indole, N-CH$_2$-(4-Cl-phenyl), fused cyclohexene with CH(Me)-CO$_2$H) | 0.31 | 6.8 |

The magnitude of a prophylactic or therapeutic dose of a compound of Formula I will, of course, vary with the nature or the severity of the condition to be treated and with the particular compound of Formula I and its route of administration. In general, the daily dose range for anti-asthmatic, anti-allergic, or anti-thrombotic use lies within the range of from about 0.01 mg to about 100 mg per kg body weight of a mammal.

The exact amount of a compound of Formula I to be used as a cytoprotective agent will depend on, inter alia, whether it is being administered to heal damaged cells or to avoid future damage, on the nature of the damaged cells (e.g., gastro-intestinal ulcerations vs. nephrotic necrosis), and on the nature of the causative agent. An example of use of a compound of Formula I to avoid future damage is coadministration with a non-steroidal anti-inflammatory drug (for example, indomethacin).

The effective daily dosage level for compounds of Formula I inducing cytoprotection in mammals, especially humans, will generally range from about 0.002 mg/kg to about 100 mg/kg, preferably from about 0.02 mg/kg to about 30 mg/kg. The dosage may be administered in single or divided individual doses.

Any suitable route of administration may be employed for providing a mammal, especially a human with an effective dosage of a compound of Formula I. For example, oral, rectal, topical, parenteral, ocular, nasal, buccal, intravenous and the like may be employed. Dosage forms include tablets, troches, dispersions, suspensions, solutions, capsules, creams, ointments, aerosols and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, or anti-allergic use is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I per kg of body weight per day. In the case where an oral composition is employed, a suitable dosage range for anti-asthmatic, or anti-allergic use is, e.g. from about 1 to about 100 mg of a compound of Formula I per kg of body weight per day, preferably from about 5 mg to about 40 mg per kg and for cytoprotective use from about 0.01 to about 100 mg (preferably from about 0.1 mg to about 30 mg and were preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser, or a powder which may be formulated as a cartridge from which the powder composition may be inhaled with the aid of a suitable device. The preferred delivery system for inhalation in a metered dose inhalation (MDI) aerosol, which may be formulated as a suspension or solution in fluorocarbon propellants.

Suitable topical formulations of compound I include transdermal devices, aerosols, creams, ointements, lotions, dusting powder, and the like.

In practical use, a compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of brining into association the active ingredient with the carrier which constitutes one or more necessary ingredients. In general, the compositions are prepared by uniformly and intimately admixing the active ingredient with liquid carriers or finely divided solid carriers or both, and the, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 2.0 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|

| | |
|---|---|
| Compound of Formula I | 25.0 |
| Microcrystalline Cellulose | 415.0 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as non-steroidal anti-inflammatory drugs (NSAIDs), peripheral analgesic agents such as zomepirac, diflunisal and the like, cyclooxygenase inhibitors leukotriene antagonists, leukotriene biosynthesis inhibitors, $H_2$-receptor antagonists, antihistaminic agents, prostaglandin antagonists, ACE inhibitors, and thromboxane synthetase inhibitors. The weight ratio of the compound of the Formula I to the second active ingredient may be varied and will depend upon the effective dose of each ingredient. Generally, an effective dose of each will be used. Thus, for example, when a compound of the Formula I is combined with a second active ingredient the weight ratio of the compound of the Formula I to the second ingredient will generally range from about 1000:1 to about 1:1000, preferably from 200:1 to 1:200. Combinations of a compound of the Formula I and other active ingredients will generally be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDS which are within the scope of this invention are those disclosed in EP No. 140,684.

Pharmaceutical compositions comprising the Formula I compounds may also contain other inhibitors of the biosynthesis of the leukotrienes such as are disclosed in EP No. 138,481 (Apr. 24, 1985), EP No. 115,394 (Aug. 8, 1984), EP No. 136,893 (Apr. 10, 1985), and EP No. 140,709 (May 8, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984), which are hereby incorporated herein by reference and others known in the art such as those disclosed in European patent application Nos. 56,172 and 61,800; and in U.K. patent specification No. 2,058,785, which are hereby incorporated herein by reference.

Pharmaceutical compositions comprising the Formula I compounds may also contain as the second active ingredient, other prostaglandin antagonists such as those disclosed in European patent application No. 11,067 (May 28, 1980) or other thromboxane antagonists such as those disclosed in U.S. Pat. No. 4,237,160. They may also contain histidine decarboxyase inhibitors such as α-fluoromethyl-histidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP No. 40,696 (Dec. 2, 1981) and like compounds, such as those disclosed in U.S. Pat. Nos. 4,283,408; 4,362,736; 4,394,509; and a pending application, U.S. Ser. No. 301,616, filed Sept. 14, 1981. The pharmaceutical compositions may also contain a $K^+/H^+$ ATPase inhibitor such as omeprazole, disclosed in U.S. Pat. No. 4,255,431, and the like. Compounds of I may also be usefully combined with most cell stabilizing agents, such as 1,3-bis(2-carboxychromon-5-yloxy)-2-hydroxypropane and related compounds described in British patent specification Nos. 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK No. 2,038,821 (e.g., UK No. 37248 and dazoxiben hydrochloride), U.S. Pat. No. 4,217,357 (e.g., UK No. 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK No.-38485), or EP No. 98,690 (e.g., CV-4251).

An embodiment of the invention is a cardiovascular composition useful for treating arterial thrombosis which comprises an antithrombotic compound of the Formula I.

A further embodiment of the invention is a cardivascular composition useful for treating arterial thrombosis which comprises: (1) the antithrombotic Formula I compound defined above; and, (ii) an angiotensin converting enzyme (ACE) inhibitor compound which is a member of the group: carboxyalkyl dipeptide derivatives; captopril [1-(3-mercapto-2-methyl-1-oxopropyl)-L-proline]; 2-[N-(S)-1-ethoxycarbonyl-3-phenylpropyl]-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)glycine; 1-(N-[(S)-1-ethoxy-carbonyl-3-phenylpropyl]-L-alanyl)-cis,-syn-octahydro-(H-indole-2-S)-carboxylic acid; 2-(N[(S)-1-ethoxy-carbonyl-3-penylpropyl]-L-alanyl)-1,2,3,4-tetrahydro-iso-isoquinoline-3(S)-carboxylic acid; and, 1-carboxy-methyl-3(S)-(1(S)-ethoxycarbonyl-3-phenylpropylamino)-2,3,4,5-tetrahydro-1H[1]-benzazepine-2-one.

In particular the class of ACE inhibitors which have been found to have a potentiating effect when used in combination with the Formula I compounds are those disclosed in U.S. Pat. No. 4,374,829, which also discloses methods for their preparation and which patent is incorporated herein by reference. Of the carboxyalkyl dipeptides disclosed in U.S. Pat. No. 4,374,829, those of particular interest in this invention are N-[1(S)-ethoxycarbonyl-3-phenylpropyl]-L-alanyl-L-proline, also known as and referred to herein as enalapril; N-[1(S)-carboxy-3-phenylpropyl]-L-alanyl-L-proline, also know and referred to herein as enalapril diacid; and, Nα-[1(S)-carboxy-3-phenylpropyl]-L-lysyl-L-proline, also known and referred to herein as lisinapril.

The combination composition of the invention can contain varying amounts of (i) the Formula I antithrombotic compound and (ii) ACE inhibitor antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The combination compositions can be administrered orally or other than orally; e.g., parenterally, by insufflation, topically, rectally, etc.; using appropriate dosage forms; e.g., tablets, capsules suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

Treatment dosage for human beings for cardiovascular use can be varied as necessary. Generally, daily dosages of the composition of the invention can range from about 6000 to about 10 mg; preferably, from about 3000 to about 20 mg.

The amount of active ingredient that may be combined with the carrier materials to produce a single dosage form for cardiovascular use will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 20 mg to about 500 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The composition of this invention inhibits platelet accumulation at the damaged endothelial surface via the Formula I compound. This inhibitory effect is potentiated by the presence of the antihypertensive compound.

Thus, the compositions of the invention are useful in treating thrombosis and are also of value in the management of acute and chronic congestive heart failure, and limitation of myocardial infarct damage.

In vivo testing of the composition of this invention in test animals (rabbits) can be used to demonstrate that this composition is pharmaceutically effective in decreasing platelet-related arterial thrombic formation.

To demonstrate the potentiation of the antihypertensive compound on the anti-thrombotic Formula I compound comprising the combination composition of the invention, the effect of these compounds on test animals (rabbits) can be determined separately and then in combination. The effect of a different class of antihypertensive agents singly and in combination with the Formula I compound of the invention can also be determined for comparative purposes. The methods employed are described in U.S. Pat. No. 4,558,037 which is hereby incorporated herein by reference.

The following examples illustrate the preparation of the compounds of the present invention without, however, limiting the same thereto.

All temperatures are in degrees Celsius.

REFERENCE COMPOUNDS 6-fluoro-1,2,3,4-tetrahydrocarbazol-1-yl-acetic acid

Following the procedure of Example 1, but using 1-(4-fluorophenyl)hydrazine hydrochloride and ethyl-2-cyclohexanone acetate as starting materials, the title compound was prepared.

M.P. 124°–126° C.

REFERENCE COMPOUNDS

9-[1-(2-p-chlorophenyl)ethyl]-6-fluoro-1,2,3,4-tetrahydrocarbazol-1-yl-acetic acid Following the procedure of Example 2, but using 1-[2-(4-chlorophenyl)ethyl]-1-(4-fluorophenyl)hydrazine hydrochloride and ethyl 2-cyclohexanone acetate as starting materials, the title compound was prepared.

| Empirical Formula: $C_{22}H_{21}NFClO_2$ | | |
|---|---|---|
| C | H | N |
| Calculated 68.48 | 5.49 | 3.63 |
| Found 68.15 | 5.70 | 3.65 |

REFERENCE COMPOUNDS 6-fluoro-9-isopropyl-1,2,3,4-tetrahydrocarbazol-1-yl-acetic acid Following the procedure of Example 1, but using 1-(2-propyl)-1-(4-fluorophenyl)hydrazine hydrochloride and ethyl 2-cyclohexanone acetate as starting materials, the title compound was prepared.

Empirical Formula: $C_{17}H_{20}NFO_2$.

M.P. 144°–144.5° C.

EXAMPLE 1

9-p-chlorobenzyl-6-fluoro-1,2,3,4-tetrahydrocarbazol-1-yl-acetic acid

Step I

To 3.50 g of 1-(4-chlorobenzyl)-1-(4-fluorophenyl)-hydrazine hydrochloride in 70 cc of isopropanol was added 2.23 g of ethyl 2-cyclohexanone acetate. The reaction was refluxed under nitrogen for 16 hours. The resulting reaction mixture was then evaporated to dryness and the residue suspended in ether. The solid material was then filtered. The ether filtrate was washed with water, dried and evaporated. The resulting syrup was chromatographed on silica gel to give 2.8 g (42%).

Step II

To 1.59 g of ethyl ester from step I in 10 cc of methanol was added 10 cc of water and 420 mg of potassium hydroxide. The resulting solution was refluxed for 4 hours. Upon cooling the reaction mixture was then acidified with HCl (1N). The resulting precipitate was filtered and washed with water. Analytically pure material was prepared by trituration the solid with a mixture of hexane/ethyl acetate (9:1) followed by filtration and drying on a high vacuum pump to give 1.24 g of the title compound (89%).

| Analysis calculated for $C_{21}H_{19}NClFO_2$ | | | | |
| --- | --- | --- | --- | --- |
| | C | H | N | Cl | F |
| Calculated | 67.83 | 5.15 | 3.77 | 9.53 | 5.11 |
| Found | 67.88 | 5.47 | 3.63 | 9.52 | 5.12 |

EXAMPLE 2

3-[9-p-chlorobenzyl-6-fluoro-1,2,3,4-tetrahydrocarbazol-1-yl]-propanoic acid

Following the procedure of Example 1, but using 1-(4-chlorobenzyl)-1-(4-fluorophenyl)hydrazine hydrochloride and methyl-2-cyclohexanone propionate as starting materials, the title compound was prepared.

| Empirical formula: $C_{22}H_{21}ClFNO_2$ | | | |
| --- | --- | --- | --- |
| | C | H | N |
| Calculated | 68.48 | 5.49 | 3.63 |
| Found | 68.26 | 5.57 | 3.60 |

EXAMPLE 3

3-[9-p-chlorobenzyl-6-methoxy-1,2,3,4-tetrahydrocarbazol-1-yl]-propanoic acid

Following the procedure of Example 1, but using 1-(4-chlorobenzyl)-1-(4-methoxyphenyl)hydrazine hydrochloride and methyl-2-cyclohexanone propionate as starting materials, the title compound was prepared.

| Empirical formula: $C_{22}H_{22}ClNO_3$ | | | |
| --- | --- | --- | --- |
| | C | H | N | Cl |
| Calculated | 69.43 | 6.08 | 3.52 | 8.91 |
| Found | 69.24 | 5.98 | 3.60 | 8.85 |

EXAMPLE 4

9-p-chlorobenzyl-6-methoxy-1,2,3,4-tetrahydrocarbazol-1-yl-acetic acid

Following the procedure of Example 1, but using 1-(4-chlorobenzyl)-1-(4-methoxyphenyl)hydrazine hydrochloride and ethyl-2-cyclohexanone acetate as starting materials, the title compound was prepared.
M.P. 152°–153° C.

EXAMPLE 5

2-[9-p-chlorobenzyl-6-fluoro-1,2,3,4-tetrahydrocarbazol-1-yl]ethanol 1.10 g of 9-p-chlorobenzyl-6-fluoro-1,2,3,4-tetrahydrocarbazo-1-yl-acetic acid ethyl ester was dissolved in 500 ml dry tetrahydrofuran and the reaction was cooled at 0° C. and one equivalent of lithium aluminum hydride (LAH) was added portion wise. The reaction was allowed to warm up to room temperature and stirred for 16 hrs. The reaction mixture was quenched with $NH_4Cl$ (aq.). Ethyl acetate was added (100 ml) and the organic phase separated, washed with water and brine, dried and evaporated. The product was isolated by column chromatography.
M.P. 98.0°–98.5° C.

EXAMPLE 6

3-[9-p-chlorobenzyl-6-methoxy-1,2,3,4-tetrahydrocarbazol-1-yl]-propanol

Following the procedure of Example 5, but using 3-[9-p-chlorobenzyl-6-methoxy-1,2,3,4-tetrahydrocarbazo-1-yl]-propanoic acid methyl ester from Example 3 as starting material, the title compound was prepared.

| Empirical formula: $C_{23}H_{26}ClNO_2$ | | | |
| --- | --- | --- | --- |
| | C | H | N |
| Calculated | 71.95 | 6.83 | 3.65 |
| Found | 71.86 | 6.65 | 3.81 |

EXAMPLE 7

(−)9-p-chlorobenzyl-6-fluoro-1,2,3,4-tetrahydrocarbazol-1-yl-acetic acid

Step I 10.0 g of 9-p-chlorobenzyl-6-fluoro-1,2,3,4-tetrahydrocarbazo-1-yl-acetic acid from Example 1 was dissolved in a mixture of hot (refluxing acetonitrile (150 cc), and ethanol (25 cc) and 4.4 g of d(+) ephedrine was added. The reflux was continued for 15 min. and the hot solution was filtered and allowed to cool to room temperature. Crystals separated from the solution and were separated by filtration. After three recrystalization from acetonitrile 3.9 g of the pure salt was obtained.

Step II 3.9 g of pure salt from step I was dissolved in 200 cc of methanol and acidified using 1N hydrochloric acid. Water was added and the crystals were separated by filtration and dried under vacuum. Upon trituration with hexane ethyl acetate mixture (9:1) the title compound was prepared.
αD=−42.5 (methanol), M.P. 151°–151.5° C.

EXAMPLE 8

(+)9-p-Chlorobenzyl-6-fluoro-1,2,3,4-tetrahydrocarbazol-1-yl-acetic acid

Following the method of Example 7, but using 1(−) ephedrine and 9-p-chlorobenzyl-6-fluoro-1,2,3,4-tetrahydrocarbazo-1-yl-acetic acid as starting material, the title compound was prepared.
αD=+43.0 (methanol), M.P. 150°–150.5° C.

EXAMPLE 9

9-benzyl-6-fluoro-1,2,3,4-tetrahydrocarbazol-1-ylacetic acid

Following the procedure of Example 1, but using 1-(benzyl)-1-(4-fluorophenyl)hydrazine hydrochloride and ethyl 2-cyclohexanone acetate as starting materials, the title compound was prepared.

| Analysis calculated for $C_{21}H_{20}NFO_2$ | | |
| --- | --- | --- |
| | C | H | N |
| Calculated | 74.76 | 5.98 | 4.15 |
| Found | 74.95 | 6.07 | 3.90 |

EXAMPLE 10

9-p-methoxybenzyl-6-fluoro-1,2,3,4-tetrahydrocarbazol-1-yl-acetic acid

Following the procedure of Example 1, but using 1-(4-methoxybenzyl)-1-(4-fluorophenyl)hydrazine hydrochloride and ethyl 2-cyclohexanone acetate as starting materials, the title compound was prepared.

| Analysis calculated for $C_{22}H_{22}NFO_3$ | | | |
|---|---|---|---|
| | C | H | N |
| Calculated | 71.92 | 6.04 | 3.91 |
| Found | 71.70 | 6.22 | 4.05 |

EXAMPLE 11

9-(3,4-dichloro)benzyl-6-fluoro-1,2,3,4-tetrahydrocarbazol-1-yl-acetic acid

Following the procedure of Example 1, but using 1-(3,4-dichlorobenzyl)-1-(4-fluorophenyl)hydrazine hydrochloride and ethyl 2-cyclohexanone acetate as starting materials, the title compound was prepared.

| Analysis calculated for $C_{21}H_{18}NCl_2FO_2$ | | | |
|---|---|---|---|
| | C | H | N |
| Calculated | 62.08 | 4.47 | 3.45 |
| Found | 61.96 | 4.71 | 3.67 |

EXAMPLE 12

9-[1-(1-phenyl)ethyl]-6-fluoro-1,2,3,4-tetrahydrocarbazol-1-yl-acetic acid

Following the procecure of Example 1, but using 1-[1-(1-phenyl)ethyl]-1-(4-fluorophenyl)hydrazine hydrochloride and ethyl 2-cyclohexanone acetate as starting materials, the title compound was prepared.

| | C | H | N | F |
|---|---|---|---|---|
| Calculated | 75.19 | 6.31 | 3.99 | 5.41 |
| Found | 75.18 | 6.05 | 4.11 | 5.51 |

EXAMPLE 13

9-p-chlorobenzyl-1,2,3,4-tetrahydrocarbazol-1-yl-acetic acid

Following the procedure of Example 1, but using 1-(4-chlorobenzyl)-1-(phenyl)hydrazine hydrochloride and ethyl 2-cyclohexanone acetate as starting materials, the title compound was prepared.

| Empirical Formula: $C_{21}H_{20}NClO_2$ | | | |
|---|---|---|---|
| | C | H | N | Cl |
| Calculated | 71.28 | 5.70 | 3.96 | 10.02 |
| Found | 70.7n | 5.90 | 3.82 | 10.23 |

EXAMPLE 14

9-p-chlorobenzyl-6-chloro-1,2,3,4-tetrahydrocarbazol-1-yl-acetic acid

Following the procedure of Example 1, but using 1-(4-chlorobenzyl)-1-(4-chlorophenyl)hydrazine hydrochloride and ethyl-2-cyclohexanone acetate as starting materials, the title compound was prepared.

| Empirical Formula: $C_{21}H_{19}NCl_2O_2$ | | | |
|---|---|---|---|
| | C | H | N | Cl |
| Calculated | 69.96 | 4.93 | 3.61 | 18.26 |
| Found | 65.20 | 5.16 | 3.38 | 18.04 |

EXAMPLE 15

9-p-chlorobenzyl-8-methyl-1,2,3,4-tetrahydrocarbazol-1-yl-acetic acid

Following the procedure of Example 1, but using 1-(4-chlorobenzyl)-1-(2-methylphenyl)hydrazine hydrochloride and ethyl-2-cyclohexanone acetate as starting materials, the title compound was prepared.

| Empirical Formula: $C_{22}H_{22}NClO_2$ | | | |
|---|---|---|---|
| | C | H | N | Cl |
| Calculated | 71.83 | 6.03 | 3.81 | 9.64 |
| Found | 72.19 | 6.23 | 4.12 | 9.84 |

EXAMPLE 16

6-bromo-9-p-chlorobenzyl-1,2,3,4-tetrahydrocarbazol-1-yl-acetic acid

Following the procedure of Example 1, but using 1-(4-chlorobenzyl)-1-(4-bromophenyl)hydrazine hydrochloride and ethyl 2-cyclohexanone acetate as starting materials, the title compound was prepared.

| Empirical formula: $C_{21}H_{19}BrClNO_2$ | | | | |
|---|---|---|---|---|
| | C | H | N | Br | Cl |
| Calculated | 58.29 | 4.43 | 3.24 | 18.46 | 8.19 |
| Found | 58.49 | 4.60 | 3.44 | 18.50 | 8.27 |

EXAMPLE 17

9-p-chlorobenzyl-6-methyl-1,2,3,4-tetrahydrocarbazol-1-yl-acetic acid

Following the procedure of Example 1, but using 1-(4-chlorobenzyl)-1-(4-methylphenyl)hydrazine hydrochloride and ethyl 2-cyclohexanone acetate as starting materials, the title compound was prepared.

| Empirical formula: $C_{22}H_{22}ClNO_2$ | | | |
|---|---|---|---|
| | C | H | N | Cl |
| Calculated | 71.83 | 6.03 | 3.81 | 9.64 |
| Found | 71.72 | 6.14 | 3.77 | 9.88 |

EXAMPLE 18

2-[9-p-chlorobenzyl-6-fluoro-1,2,3,4-tetrahydrocarbazol-1-yl-]propanoic acid

Following the procedure of Example 1, but using 1-(4-chlorobenzyl)-1-(4-fluorophenyl)hydrazine hydrochloride and methyl 2-(2-cyclohexanone)propionate as starting materials, the title compound was prepared.
M.P. 203°–205° C.

EXAMPLE 19

9-p-chlorobenzyl-8 fluoro-1,2,3,4-tetrahydrocarbazol-1-yl-acetic acid

Following the procedure of Example 1, but using 1-(4-chlorobenzyl)-1-(2-fluorophenyl)hydrozine hydrochloride and ethyl 2-cyclohexanone acetate as starting materials, the title compound was prepared.
M.P. 228°–229° C.

EXAMPLE 20

3-[(α and β)-t-butyl-6-fluoro-9-(p-chlorobenzyl)-1,2,3,4-tetrahydrocarbazol-1-yl]acetic acid Following the procedure of Example 1 but using 4-t-butyl-2-carbomethoxymethyl cyclohexanone and 1-(4-chlorobenzyl)-4-fluorophenylhydrazine hydrochloride as the starting materials, the title compound was prepared.
M.P. 210°–211° C.

EXAMPLE 21

9-p-chlorobenzyl-5-fluoro-1,2,3,4-tetrahydrocarbazol-1-yl-acetic acid and 9-p-chlorobenzyl-7-fluoro-1,2,3,4-tetrahydrocarbazol-1-yl-acetic acid (mixture)

Following the procedure of Example 1, but using 1-(4-chlorobenzyl)-1-(3-fluorophenyl)hydrazine hydrochloride and ethyl 2-cyclohexanone acetate as starting materials, the title compounds were prepared.
Empirical Formula: $C_{21}H_{19}NClFO_2$.
M.P. 211°–219° C.

EXAMPLE 22

9-p-chlorobenzyl-5,7-dichloro-1,2,3,4-tetrahydrocarbazol-1-yl-acetic acid

Following the procedure of Example 1, but using 1-(4-chlorobenzyl)-1-(3,5-dichlorophenyl)hydrozine hydrochloride and ethyl 2-cyclohexanone acetate as starting material, the title compound was prepared.
Empirical formula: $C_{21}H_{18}NCl_3O_2$.
M.P. 204°–206° C.

EXAMPLE 23

9-p-chlorobenzyl-6,8-dichloro-1,2,3,4-tetrahydrocarbazol-1-yl-acetic acid

Following the procedure of Example 1, but using 1-(4-chlorobenzyl)-1-(2-4-dichlorophenyl)hydrozine hydrochloride and ethyl 2-cyclohexanone acetate as starting materials, the title compound was prepared.
Empirical formula: $C_{21}H_{18}NCl_3O_2$.
M.P. 203;20 –204° C.

EXAMPLE 24

9-p-Chloro-benzyl-6-isopropyl-1,2,3,4-tetrahydrocarbazol-1-yl-acetic acid

Following the procedure of Example 1, but using 1(4-chlorobenzyl)-1-(4-isopropylphenyl)hydrazine hydrochloride and ethyl 2-cyclohexanone acetate as starting material, the title compound was prepared.

| Empirical Formula: $C_{24}H_{26}ClNO_2$ | | | |
|---|---|---|---|
| | C | H | N | Cl |
| Calc: | 72.81 | 6.62 | 3.54 | 8.95 |
| Found: | 72.83 | 7.09 | 3.61 | 9.21 |

EXAMPLE 25

9-p-Chlorobenzyl-6-tert-butyl-1,2,3,4-tetrahydrocarbazol-1-yl-acetic acid

Following the procedure of Example 1, but using 1-(4-chlorobenzyl)-1-(4-tert-butylphenyl)hydrazine hydrochloride and ethyl2-cyclohexanone acetate as starting materials, the title compound was prepared.

| Empirical Formula: $C_{25}H_{28}ClNO_2$ | | | |
|---|---|---|---|
| | C | H | N | Cl |
| Calc. | 73.24 | 6.88 | 3.42 | 8.65 |
| Found: | 73.21 | 7.32 | 3.10 | 8.26 |

EXAMPLE 26

9-p-Chlorobenzyl-6-trifluoromethyl-1,2,3,4-tetrahydrocarbazol-1-yl-acetic acid Following the procedure of Example 1, but using 1-(4-chlorobenzyl)-1-(4-trifluoromethylphenyl)hydrazine hydrochloride and ethyl 2-cyclohexanone acetate as starting materials, the title compound was prepared.
m.p. 167°–168° C.

EXAMPLE 27

9-p-Chlorobenzyl-6-methylthio-1,2,3,4-tetrahydrocarbazol-1-yl-acetic acid

Following the procedure of Example 1, but using 1-(4-chlorobenzyl)-1-(4-methylthiophenyl)hydrazine hydrochloride and ethyl 2-cyclohexanone acetate as starting materials, the title compound was prepared.

| Empirical Formula: $C_{22}H_{22}ClNO_2S$ | | | | |
|---|---|---|---|---|
| | C | H | N | S | Cl |
| Calc: | 66.07 | 5.54 | 3.50 | 8.02 | 8.86 |
| Found: | 66.27 | 5.83 | 3.38 | 8.00 | 8.70 |

EXAMPLE 28

9-p-Chlorobenzyl-6-methylsulfinyl-1,2,3,4-tetrahydrocarbazol-1-yl-acetic acid

Step I

To 498 mg of ethyl 9-p-chlorobenzyl-6-methylthio-1,2,3,4-tetrahydrocarbazol-1-yl-acetate from Example 27, Step I, in 10 cc of methylene chloride was added 300 mg of m-chloro perbenzoic acid. The resulting mixture was stirred for 1.5 hours at room temperature. The reaction mixture was diluted with ether and washed consecutively with a solution of sodium bicarbonate, water and brine. The crude product obtained after evaporation of the organic layer was purified on silica gel by flash chromatography eluting with 20% hexane/ethyl acetate and yielded 420 mg (82%) of the pure sulfoxide derivative.

Step II

Following the procedure of Example 1, Step II, but using the ethyl ester from Step I, there was obtained the title compound. m.P. 105°–107° C.

Empirical Formula: $C_{22}H_{22}ClNO_3S$

|  | C | H | N | S | Cl |
|---|---|---|---|---|---|
| Calc: | 63.53 | 5.33 | 3.37 | 7.71 | 8.52 |
| Found: | 63.31 | 5.03 | 2.94 | 7.69 | 8.48 |

EXAMPLE 29

9-p-Chlorobenzyl-6-methylsulfonyl-1,2,3,4-tetrahydrocarbazol-1-yl-acetic acid

Step I

To 439 mg of ethyl 9-p-chlorobenzyl-6-methylsulfinyl-1,2,3,4-tetrahydrocarbazol-1-yl-acetate from Example 28, Step I, in 10 cc of methylene chloride was added 353 mg of m-chloro perbenzoic acid. The resulting mixture was stirred for 18 hours at room temperature. The reaction mixture was diluted with ether and washed consecutively with a solution of sodium bicarbonate, water and brine. The crude product obtained after evaporation of the organic layer was purified on silica gel by flash chromatography eluting with 30% hexane/ethyl acetate and yielded 200 mg (42%) of the pure sulfone derivative.

Step II

Following the procedure of Example 1, Step II, but using the ethyl ester from Step I, there was obtained the title compound. m.p. 101°–102° C.

EXAMPLE 30

9-p-Chlorobenzyl-8-isopropyl-1,2,3,4-tetrahydrocarbazol-1-yl-acetic acid

Following the procedure of Example 1, but using 1-(4-chlorobenzyl)-1-(2-isopropylphenyl)hydrazine hydrochloride and ethyl 2-cyclohexanone acetate as starting materials, the title compound was prepared.

Empirical Formula: $C_{24}H_{26}ClNO_2$

|  | C | H |
|---|---|---|
| Calc: | 72.81 | 6.62 |
| Found: | 72.59 | 6.90 |

EXAMPLE 31

9-p-Chlorobenzyl-8-methylthio-1,2,3,4-tetrahydrocarbazol-1-yl-acetic acid

Following the procedure of Example 34, but using 1-(2-methylthiophenyl)hydrazine hydrochloride and ethyl 2-cyclohexanone acetate as starting materials, the title compound was prepared. m.p. 141°–142° C.

EXAMPLE 32

9-p-Chlorobenzyl-8-methylsulfinyl-1,2,3,4-tetrahydrocarbazol-1-yl-acetic acid Following the procedure of Example 28, but using the ethyl ester from Example 31, Step II, there was obtained with the title compound. m.p. 119°–120.5° C.

EXAMPLE 33

9-p-Chlorobenzyl-6-fluoro-3-methyl-1,2,3,4-tetrahydrocarbazol-1-yl-acetic acid Following the procedure of Example 1, but using 1-(4-chlorobenzyl)-1-(4-fluorophenyl)hydrazine hydrochloride and ethyl 4-methyl-2-cyclohexanone acetate as starting materials, the title compound was prepared. m.p. 205°–206° C.

Empirical Formula: $C_{22}H_{21}FClNO_2$

|  | C | H | N | Cl |
|---|---|---|---|---|
| Calc: | 68.48 | 5.49 | 3.63 | 9.19 |
| Found: | 68.80 | 5.50 | 3.30 | 9.47 |

EXAMPLE 34

9-p-Chlorobenzyl-6,8-difluoro-1,2,3,4-tetrahydrocarbazol-1-yl-acetic acid

Step I

To 114 g of 1-(2,4-difluorophenyl)hydrazine hydrochloride in 350 cc of 2-propanol containing 40 cc of acetyl chloride was added 138 g of ethyl 2-cyclohexanone acetate. The reaction was refluxed under nitrogen for 2 days. After cooling, 200 cc of ether was added and the precipitate filtered. The filtrate was evaporated to dryness. The resulting residue was dissolved in a (1:1) mixture of ether/ethyl acetate and consecutively washed with water, sodium bicarbonate solution and brine. The organic layer was dried over sodium sulfate and evaporated to dryness. The crude product was passed through a silica gel bed eluting with 5% ethyl acetate/hexane to yield 84 g of a 1:2 mixture of ethyl and isopropyl esters.

Step II 84 g of esters from Step I was dissolved in 250 cc of methanol and 400 cc of sodium hydroxide (1N) was added and refluxed 4 hours. After cooling, the reaction mixture was washed with a (1:1) mixture of ether/hexane and the aqueous layer was acidified with HCl (1N). The resulting precipitate was filtered, washed with water and air dried to afford 50 g of 6,8-difluoro-1,2,3,4-tetrahydrocarbazol-1-yl-acetic acid.

Step III

A solution of 11:1 g of acid from Step II in 100 cc of THF was added portionwise 10.3 g of potassium tert-butoxide. The resulting mixture was stirred for 45 min. at room temperature and 10.3 g p-chlorobenzyl bromide was added portionwise. the reaction mixture was stirred 18 hours at room temperature. The resulting mixture was diluted with 100 cc of water and washed with hexane. The aqueous layer was acidified with HCl (1N) and the resulting precipitate filtered washed with water and air-dried to afford 9.4 g of the title compound. m.p. 168.5°–170° C.

EXAMPLE 35

9-p-Chlorobenzyl-6,8-dimethyl-1,2,3,4-tetrahydrocarbazol-1-yl-acetic acid

Following the procedure of Example 34, but using 1-(2,4-dimethylphenyl)hydrazine hydrochloride and ethyl 2-cyclohexanone acetate in Step I as starting materials, the title compound was prepared. m.p. 187°–188° C.

EXAMPLE 36

9-p-Chlorobenzyl-6-methoxy-8-methyl-1,2,3,4-tetrahydrocarbazol-1-yl-acetic acid

Following the procedure of Example 34, but using 1-(4-methoxy-2-methylphenyl)hydrazine hydrochloride and ethyl 2-cyclohexanone acetate as starting materials, the title compound was prepared. m.p. 188°–188.5° C.

EXAMPLE 37

(−)-9-p-Chlorobenzyl-6,8-difluoro-1,2,3,4-tetrahydrocarbazol-1-yl-acetic acid

Following the method of Example 7, but using d(+)ephedrine and 9-p-chlorobenzyl-6,8-difluoro-1,2,3,4-tetrahydrocarbazol-1-yl-acetic acid from Example 34 as starting materials, the title compound was prepared. From Example 34 $[\alpha]_D = -64.3°$ (methanol) m.p. 130°–131° C.

EXAMPLE 38

(+)-9-p-Chlorobenzyl-6,8-difluoro-1,2,3,4-tetrahydrocarbazol-1-yl-acetic acid

Following the method of Example 37, but using l(−)ephedrine, the title compound was prepared. $[\alpha]_D = +61.5°$ (methanol) m.p. 129.5°–130° C.

EXAMPLE 39

(−)-9-p-Chlorobenzyl-8-methyl-1,2,3,4-tetrahydrocarbazol-1-yl-acetic acid

Following the method of Example 7, but using d(+)ephedrine and 9-p-chlorobenzyl-8-methyl-1,2,3,4-tetrahydrocarbazol-1-yl-acetic acid from Example 15 as starting materials, the title compound was prepared. $[\alpha]_D = -51.6°$ (methanol) m.p. 196°–198° C.

EXAMPLE 40

(+)-9-p-Chlorobenzyl-8-methyl-1,2,3,4-tetrahydrocarbazol-1-yl-acetic acid

Following the method of Example 39, but using l(−)ephedrine, the title compound was prepared. $[\alpha]_D = +45.9°$ (methanol) m.p. 195°–197° C.

EXAMPLE 41

(−)-9-p-Chlorobenzyl-8-fluoro-1,2,3,4-tetrahydrocarbazol-1-yl-acetic acid

Following the method of Example 7, but using d(+)ephedrine and 9-p-chlorobenzyl-8-fluoro-1,2,3,4-tetrahydrocarbazol-1-yl-acetic acid from Example 19 as starting materials, the title compound was prepared. $[\alpha]_D = -62.1°$ (methanol) m.p. 74°–75° C.

EXAMPLE 42

(+)-9-p-Chlorobenzyl-8-fluoro-1,2,3,4-tetrahydrocarbazol-1-yl-acetic acid

Following the method of Example 41, but using l(−)ephedrine, the title compound was prepared. $[\alpha]_D = +65.2°$ (methanol) m.p. 94°–94.5° C.

EXAMPLE 43

2-(9-p-Chlorobenzyl-6,8-difluoro-1,2,3,4-tetrahydrocarbazol-1-yl)ethanol

Following the procedure of Example 5, but using a mixture of 9-p-chlorobenzyl-6,8-difluoro-1,2,3,4-carbazol-1-yl-acetic acid ethyl and isopropyl esters from Example 34 as starting materials, the title compound is obtained.

EXAMPLE 44

(−) or (+) 2-(9-p-Chlorobenzyl-6,8-difluoro-1,2,3,4-tetrahydrocarbazol-1-yl)ethanol Following the procedure of Example 5, but using (−) or (+) 9-p-chlorobenzyl-6,8-difluoro-1,2,3,4-tetrahydrocarbazol-1-yl-acetic acid from Example 37 or 38 as starting material, the title compounds are obtained.

EXAMPLE 45

9-o-Chlorobenzyl-6,8-difluoro-1,2,3,4-tetrahydrocarbazol-1-yl-acetic acid

A solution of 200 mg of 6,8-difluoro-1,2,3,4-tetrahydrocarbazol-1-yl-acetic acid from Example 34 step II in 8 cc of DMF was added portionwise 40 mg of sodium hydride. The resulting mixture was stirred for 30 minutes at room temperature and 185 mg of o-chloro-benzyl bromide was then added. After stirring overnight at room temperature, the resulting mixture was diluted with water and washed with ether. The aqueous layer was acidified with (1N) HCl and extracted with ether. The ethereal layer was washed with brine, dried over $Na_2SO_4$ and evaporated to dryness. The crude product was purified on preparative plates (silica gel) eluting with $CHCl_3$:MeOH:$NH_4OH$ (8:4:1) to yield 98 mg of pure title product. m.p. 197°–198° C.

EXAMPLE 46

9-(2,4-Dichlorobenzyl)-6,8-difluoro-1,2,3,4-tetrahydrocarbazol-1-yl-acetic acid

Following the procedure of Example 45, but substituting 2,4-dichlorobenzyl chloride for o-chlorobenzyl bromide as starting material, the title compound was obtained; m.p. 160°–161° C.

EXAMPLE 47

9-p-Methylthiobenzyl-6,8-difluoro-1,2,3,4-tetrahydrocarbazol-1-yl-acetic acid

Following the procedure of Example 45, but substituting p-methylthiobenzyl chloride for o-chlorobenzyl bromide as starting material, the title compound was obtained. m.p. 145°–146° C.

EXAMPLE 48

9-p-Methylsulfinylbenzyl-6,8-difluoro-1,2,3,4-tetrahydrocarbazol-1-yl-acetic acid Following the procedure of Example 45, but substituting p-metylsulfinylbenzyl chloride for o-chlorobenzyl bromide as starting material, the title compound was obtained. m.p. 186°–188° C.

EXAMPLE 49

9-p-Methylsulfonylbenzyl-6,8-difluoro-1,2,3,4-tetrahydrocarbazol-1-yl-acetic acid To a cold solution of (0° C.) of 4.0 g of 6,8-difluoro-1,2,3,4-tetrahyrdrocarbazol-1-yl-acetic acid in 75 cc of tetrahydrofuran was added dropwise 46.3 cc of a solution of KHMDS in toluene (0.684M) and stirred for 10 minutes. To the resulting cold (0° C.) solution was added dropwise 3.7 g of a solution of p-methylsulfonylbenzyl chloride in 12 cc of tetrahydrofuran. The reaction mixture was then stirred at room temperature for 2 hours. The reaction mixture was diluted with water and washed with ether. The aqueous layer was acidified with (1N) HCl and extracted with ethyl acetate. The organic layer was washed with brine, dried over $Na_2SO_4$ and evaporated to dryness. The residue was triturated with a mixture of ethyl acetate:hexane (3:7) and filtered to yield 5.1 g of the title product. m.p. 217°–219° C.

EXAMPLE 50

(−)9-p-Methylsulfonylbenzyl-6,8-difluoro-1,2,3,4-tetrahydrocarbazol-1-yl acetic acid Following the method of Example 7, but using 1(−) ephedrine and 9-p-methylsulfonylbenzyl-6,8-difluoro-1,2,3,4-tetrahydrocarbazol-1-yl-acetic acid from Example 49 as starting materials, the title compound was prepared $[\alpha]_D = -56.°$ C. (methanol).

EXAMPLE 51

(+)9-p-Methylsulfonylbenzyl-6,8-difluoro-1,2,3,4-tetrahydrocarbazol-1-yl-acetic acid Following the method of Example 50, but using d(+) ephedrine, the title compound was prepared $[\alpha]_D = +56.0°$ (methanol).

EXAMPLE 52

9-p-Trifluoromethylbenzyl-6,8-difluoro-1,2,3,4-tetrahydrocarbazol-1-yl-acetic acid Following the procedure of Example 45, but substituting p-trifluoromethylbenzyl bromide for o-chlorobenzyl bromide as starting material, the title compound was obtained. m.p. 176°–177° C.

EXAMPLE 53

9-p-Fluorobenzyl-6,8-difluoro-1,2,3,4-tetrahydrocarbazol-1-yl-acetic acid

Following the procedure of Example 45, but substituting p-fluorobenzyl bromide for o-chlorobenzyl bromide as starting material, the title compound was obtained. m.p. 195°–196° C.

EXAMPLE 54

9-m-Chlorobenzyl-6,8-difluoro-1,2,3,4-tetrahydrocarbazol-1-yl-acetic acid

Following the procedure of Example 45, but substituting m-chlorobenzyl bromide for o-chlorobenzyl bromide as starting material, the title compound was obtained. m.p. 188°–189° C.

EXAMPLE 55

9-p-Carbomethoxybenzyl-6,8-difluoro-1,2,3,4-tetrahydrocarbazol-1-yl-acetic acid

Following the procedure of Example 45, but substituting p-carbomethoxybenzyl chloride for o-chlorobenzyl bromide as starting material, the title compound was obtained. m.p. 169°–170° C.

EXAMPLE 56

9-p-Dimethylcarboxamidobenzyl-6,8-difluoro-1,2,3,4-tetrahydrocarbazol-1-yl-acetic acid Following the procedure of Example 45, but substituting p-dimethylcarboxamidobenzyl chloride for o-chlorobenzyl bromide as starting material, the title compound was obtained. m.p. 208°–210° C.

EXAMPLE 57

9-p-Acetylbenzyl-6,8-difluoro-1,2,3,4-tetrahydrocarbazol-1-yl-acetic acid

Following the procedure of Example 45, but substituting p-acetylbenzyl chloride for o-chlorobenzyl bromide as starting material, the title compound was obtained. m.p. 163°–164° C.

EXAMPLE 58

9-p-Dimethylaminosulfonylbenzyl-6,8-difluoro-1,2,3,4-tetra-hydro carbazol-1-acetic acid Following the procedure of Example 45, but substituting p-dimethylaminosulfonylbenzyl chloride for o-chloro benzyl bromide as starting material, the title compound was obtained m.p. 200°–202° C.

EXAMPLE 59

9-p-Acetamidobenzyl-6,8-difluoro-1,2,3,4-tetra-hydro carbazol-1-yl-acetic acid

Step I

Following the procedure of Example 45, but substituting p-nitrobenzyl bromide for o-chlorobenzyl chloride as starting material, the crude 9-p-nitrobenzyl-6,8-difluoro-1,2,3,4-tetrahydrocarbazol-1-yl-acetic acid was obtained.

Step II

The crude acid from step I was dissolved in ether and esterified with diazomethane. The reaction was monitored by TLC. The resulting solution was evaporated to dryness and the oily residue was chromatographed on flash silica gel column eluting with ethylacetate:hexane mixture (1:4) to afford 4.1 g (from 4.1 g of 6,8-difluoro-1,2,3,4-tetra-hydro-carbazol-1-yl-acetic acid used in step I) of pure methyl 9-p-nitrobenzyl-6,8-difluoro-1,2,3,4-tetrahydro-carbazol-1-yl-acetate.

Step III

To a solution of 4.0 g of ester from step II in 40 cc of ethyl acetate and 70 cc of ethanol was added 400 mg of Pd/c (10%) and the resulting mixture was hydrogenated on the parr for 90 minutes under 30 psi of hydrogen. The reaction mixture was filtered on celite and the filtrate was evaporated to dryness leaving 3.5 g of the aminoester derivative as a foam.

Step IV

To a solution of 595 mg of the aminoester derivative from step III and 0.325 cc of triethylamine in 10 cc of tetrahydrofuran was added dropwise 0.132 cc of acetyl chloride and the resulting mixture was stirred for 30 minutes at room temperature. The reaction mixture was diluted with water and ether. The ether layer was decanted, washed with brine, dried over $Na_2SO_4$ and evaporated to dryness. The residue was triturated with a mixture of ethylacetate:hexane (3:7) and filtered to afford 600 mg of the acetamidoester derivative.

Step V

A solution of 600 mg of the acetamidoester derivative from step IV in a 20 cc mixture of (2.5N) NaOH:ethanol (1:1) was stirred for 30 minutes at room temperature. The reaction mixture was acidified with (1N) HCl and the precipitate was filtered, washed with water and air-dried to afford 500 mg of the title product m.p. 237°–239° C.

EXAMPLE 60

9-p-Methylsulfonamidobenzyl-6,8-difluoro-1,2,3,4-tetrahydro carbazol-1-yl-acetic acid Following the procedure of Example 59, step IV and step V, but substituting methanesulfonyl chloride for acetyl chloride as starting material, the title produce was obtained m.p. 196°–198° C.

EXAMPLE 61

9-p-Methylureidobenzyl-6,8-difluoro-1,2,3,4-tetrahydrocarbazol-1-yl-acetic acid

Step I

To a solution of 538 mg of the aminoester derivative from Example 59 step III in 10 cc of tetrahydrofuran was added 0.3 cc of methylisocyanate and the resulting solution was stirred overnight. The reaction mixture was diluted with water and ether. The ether layer was decanted, washed with brine, dried over $Na_2SO_4$ and evaporated to dryness leaving the methyl ureido ester derivative.

Step II

Following the procedure of Example 59, Step V but substituting the methyl ureido ester derivative of Step I for the acetamidoester derivative as starting material, the title product was obtained m.p. 218° C. (dec).

EXAMPLE 62

9-p-Methoxybenzyl-6,8-difluoro-1,2,3,4-tetra-hydro carbazol-1-yl-acetic acid Following the procedure of Example 45, but substituting p-methoxybenzyl chloride for o-chloro benzyl bromide as starting material, the title compound was obtained m.p. 149°–151° C.

What is claimed is:

1. A compound of the formula:

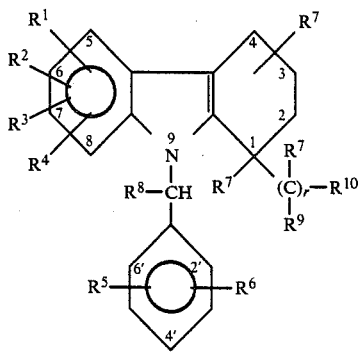

wherein:
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) —$(CH_2)_n$M
  wherein n is 0 to 3 and M is
  (a) $OR^{13}$;
  (b) halogen;
  (c) $CF_3$;
  (d) $SR^{13}$;
  (e) $COOR^{14}$;
  (f)
  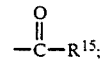
  (g)
  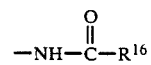
  wherein $R^{16}$ is $C_1$ to $C_6$ alkyl, benzyl or phenyl;
  (h) —$NR^{14}R^{14}$;
  (i) —$NHSO_2R^{17}$ wherein $R^{17}$ is $C_1$ to $C_6$ alkyl, 4-methylphenyl, phenyl, or $CF_3$;
  (j) —$SOR^{13}$;
  (k) —$CONR^{14}R^{14}$;
  (l) —$SO_2NR^4R^{14}$;
  (m) —$SO_2R^{13}$;
  (n) $NO_2$;
  (o) $N_3$;
  with at least one of $R^5$ and $R^6$ being —$SR^{13}$, —$S(O)R^{13}$, —$S(O)_2R^{13}$;
$R^7$ is H or alkyl of 1 to 6 carbons;
$R^8$ is H or alkyl of 1 to 6 carbon atoms;
each $R^9$ is independently H, OH, $C_1$ to $C_4$-O-alkyl or alkyl of 1 to 4 carbons;
$R^{10}$ is COOH;
r is 1 to 2;
each $R^{13}$ independently is H; $C_1$ to $C_6$ alkyl; benzyl; phenyl or substituted phenyl wherein the substituents are $C_1$ to $C_3$ alkyl, halogen, CN, $CF_3$, $COOR^{14}$, $CH_2COOR^{14}$, $C_1$ to $C_3$ alkoxy, or $C_1$ to $C_4$ perfluoroalkyl;
each $R^{14}$ is independently H, phenyl, benzyl or $C_1$ to $C_6$ alkyl; and,
each $R^{15}$ independently is H, $(CH_2)_mCOOR^{14}$ wherein m is 0 to 4, $C_1$ to $C_6$ alkyl, $CF_3$, phenyl, or substituted phenyl wherein substituted phenyl is as defined above in the definition of $R^{13}$;
or a pharmaceutically acceptable salt thereof.

2. A compound according to claim 1, wherein:
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) —$(CH_2)_n$M
  wherein n is 0 or 1 and M is as defined previously for claim 1;
with at least one of $R^5$ and $R^6$ being —$SR^{13}$, —$S(O)R^{13}$, —$S(O)_2R^{13}$;
$R^{10}$ is COOH;
r is 1 to 2.

3. A compound according to claim 2, wherein:
$R^1$, $R^2$, $R^3$, $R^4$, $R^5$ and $R^6$ are each independently selected from:
(1) hydrogen;
(2) alkyl having 1 to 6 carbon atoms;
(3) alkenyl having 2 to 6 carbon atoms;
(4) M wherein M is as defined initially for claim 1;
with at least one of $R^5$ and $R^6$ being —$SR^{13}$, —$S(O)R^{13}$, —$S(O)_2R^{13}$;
$R^{10}$ is COOH;
r is 1 or 2.

4. A compound according to claim 3, wherein:
R$^1$, R$^2$, R$^3$, R$^4$, R$^5$ and R$^6$ are each independently selected from:
(1) hydrogen;
(2) alkyl having 1 to 6 carbon atoms;
(3) M wherein M is
 (a) OR$^{13}$;
 (b) halogen;
 (c) CF$_3$;
 (d) SR$^{13}$;
 (e) COOR$^{14}$;
 (f)

(g) —SOR$^{13}$;
 (h) —CONR$^{14}$R$^{14}$;
 (i) —SO$_2$NR$^{14}$R$^{14}$;
 (j) —SO$_2$R$^{13}$;
 (k) N$_3$;
with at least one of R$^5$ and R$^6$ being —SR$^{13}$, —S(O)R$^{13}$, —S(O)$_2$R$^{13}$; each R$^9$ is independently H, or alkyl of 1 to 4 carbons;
R$^{10}$ is COOH;
r is 1.

5. A compound according to claim 1 which is:
9-p-Methylthiobenzyl-6,8-difluoro-1,2,3,4-tetrahydrocarbazol-1-yl-acetic acid;
9-p-Methylsulfinyllbenzyl-6,8-difluoro-1,2,3,4-tetrahydrocarbazol-1-yl-acetic acid;
9-p-Methylsulfonylbenzyl-6,8-difluoro-1,2,3,4-tetrahydrocarbazol-1-yl-acetic acid;
(−)9-p-Methylsulfonylbenzyl-6,8-difluoro-1,2,3,4-tetrahydrocarbazol-1-yl acetic acid;
(+)9-p-Methylsulfonylbenzyl-6,8-difluoro-1,2,3,4-tetrahydrocarbazol-1-yl acetic acid.

6. A compound according to claim 1, which is a pure optical isomer.

7. A compound according to claim 6, which is the (+)-isomer.

8. A compound according to claim 6, which is the (−)-isomer.

9. A compound of the formula:

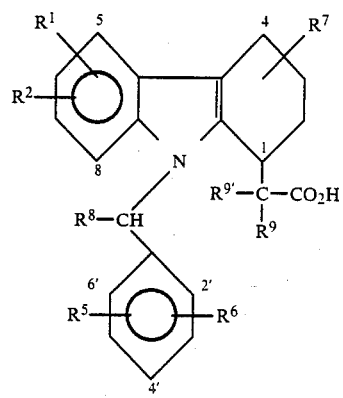

wherein:

| Compound | R$^1$ | R$^2$ | R$^5$ | R$^6$ | R$^9$, R$^{9'}$ | R$^7$ | R$^8$ |
|---|---|---|---|---|---|---|---|
| 47 | 6-F | 8-F | 4'-SMe | H | H, H | H | H |
| 48 | 6-F | H | 4'-S(O)Me | H | H, H | H | H |
| 50 | 6-F | H | 4'-S(O)$_2$Me | H | H, H | H | H |
| 61 (Ex. 48) | 6-F | 8-F | 4'-S(O)Me | H | H, H | H | H |
| 62 (Ex. 49) | 6-F | 8-F | 4'-S(O)$_2$Me | H | H, H | H | H |
| 63 (Ex. 50) | 6-F (−) isomer | 8-F | 4'-S(O)$_2$Me | H | H, H | H | H |
| 64 (Ex. 51) | 6-F (+) isomer. | 8-F | 4'-S(O)$_2$Me | H | H, H | H | H |

10. A pharmaceutical composition which comprises a compound of claim 1 and a pharmaceutically acceptable carrier.

11. A method of inhibiting leukotriene synthesis in a mammal, which comprises administering to a mammal an effective amount of a compound of claim 1.

12. A method of inhibiting leukotriene synthesis in a mammal, which comprises administering to a mammal an effective amount of a compound of claim 5.

* * * * *

UNITED STATES PATENT AND TRADEMARK OFFICE
CERTIFICATE OF CORRECTION

PATENT NO. : 4,808,608

DATED : Feb. 28, 1989

INVENTOR(S) : YVAN GUINDON, CHRISTIANE YOAKIM, JOHN W. GILLARD & YVES GIRARD

It is certified that error appears in the above-identified patent and that said Letters Patent is hereby corrected as shown below:

Please correct the Assignee to read: MERCK FROSST CANADA, INC.

Kirkland, Quebec, CANADA

Signed and Sealed this

Fifteenth Day of August, 1989

Attest:

DONALD J. QUIGG

Attesting Officer

Commissioner of Patents and Trademarks